(12) United States Patent
Zhang et al.

(10) Patent No.: US 8,492,546 B2
(45) Date of Patent: Jul. 23, 2013

(54) CO-CRYSTALS AND PHARMACEUTICAL COMPOSITIONS COMPRISING THE SAME

(75) Inventors: Yuegang Zhang, Wayland, MA (US); Patrick R. Connelly, Harvard, MA (US); Steve Johnston, Bolton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 406 days.

(21) Appl. No.: 12/675,638

(22) PCT Filed: Aug. 29, 2008

(86) PCT No.: PCT/US2008/010254
§ 371 (c)(1),
(2), (4) Date: Jul. 23, 2010

(87) PCT Pub. No.: WO2009/032198
PCT Pub. Date: Mar. 12, 2009

(65) Prior Publication Data
US 2011/0009424 A1    Jan. 13, 2011

Related U.S. Application Data

(60) Provisional application No. 60/969,023, filed on Aug. 30, 2007.

(51) Int. Cl.
*C07D 241/02* (2006.01)
(52) U.S. Cl.
USPC ........................................................ 544/407
(58) Field of Classification Search
USPC .......................................................... 544/407
See application file for complete search history.

(56) References Cited

U.S. PATENT DOCUMENTS

| | | |
|---|---|---|
| 4,499,082 A | 2/1985 | Shenvi et al. |
| 4,720,484 A | 1/1988 | Vincent et al. |
| 4,880,780 A | 11/1989 | Trainor et al. |
| 5,053,519 A | 10/1991 | Teetz et al. |
| 5,231,084 A | 7/1993 | Hock et al. |
| 5,371,072 A | 12/1994 | Webb et al. |
| 5,384,410 A | 1/1995 | Kettner |
| 5,468,858 A | 11/1995 | Berlin et al. |
| 5,484,801 A | 1/1996 | Al-Razzak et al. |
| 5,496,927 A | 3/1996 | Kolb et al. |
| 5,502,061 A | 3/1996 | Hui et al. |
| 5,559,158 A | 9/1996 | Al-Razzak et al. |
| 5,610,193 A | 3/1997 | Al-Razzak et al. |
| 5,656,600 A | 8/1997 | Abelman et al. |
| 5,656,627 A | 8/1997 | Bemis et al. |
| 5,672,582 A | 9/1997 | Veber et al. |
| 5,716,929 A | 2/1998 | Bemis et al. |
| 5,725,878 A | 3/1998 | Al-Razzak et al. |
| 5,736,520 A | 4/1998 | Bey et al. |
| 5,756,466 A | 5/1998 | Bemis et al. |
| 5,760,029 A | 6/1998 | Jadhav et al. |
| 5,807,876 A | 9/1998 | Armistead et al. |
| 5,847,135 A | 12/1998 | Bemis et al. |
| 5,849,866 A | 12/1998 | Kolb et al. |
| 5,861,267 A | 1/1999 | Su |
| 5,866,684 A | 2/1999 | Attwood et al. |
| 5,948,436 A | 9/1999 | Al-Razzak et al. |
| 5,973,111 A | 10/1999 | Bemis et al. |
| 5,990,276 A | 11/1999 | Zhang et al. |
| 6,018,020 A | 1/2000 | Attwood et al. |
| 6,025,147 A | 2/2000 | Bemis et al. |
| 6,025,516 A | 2/2000 | Ramaswamy et al. |
| 6,037,157 A | 3/2000 | Norbeck et al. |
| 6,046,195 A | 4/2000 | Haworth et al. |
| 6,054,472 A | 4/2000 | Armistead et al. |
| 6,060,469 A | 5/2000 | Baker et al. |
| 6,103,711 A | 8/2000 | Bemis et al. |
| 6,117,639 A | 9/2000 | Germann et al. |
| 6,130,315 A | 10/2000 | Kolb et al. |
| 6,143,715 A | 11/2000 | Llinas-Brunet et al. |
| 6,153,579 A | 11/2000 | Kim et al. |
| 6,172,077 B1 | 1/2001 | Curtis et al. |
| 6,183,121 B1 | 2/2001 | Kim et al. |
| 6,211,338 B1 | 4/2001 | Malcolm et al. |
| 6,225,320 B1 | 5/2001 | Kulagowski et al. |
| 6,251,583 B1 | 6/2001 | Zhang et al. |
| 6,265,380 B1 | 7/2001 | Tung et al. |
| 6,268,207 B1 | 7/2001 | Bailey et al. |

(Continued)

FOREIGN PATENT DOCUMENTS

| | | |
|---|---|---|
| DE | 3211676 | 10/1983 |
| EP | 0417721 | 3/1991 |

(Continued)

OTHER PUBLICATIONS

Almarsson et al "Crystal engineering of the composition of pharmaceutical phases. Do pharmaceutical co-crystals represent a new path to improved medicines" Chemical Comm. (2004) pp. 1889-1896.
Anonymous, VPI internet press release Sep. 7, 2004.
Anonymous, newsrx Internet article, May 31, 2004.
Arasappan, A., "Hepatitis C Virus NS3-4A Serine Protease Inhibitors: SAR of P'2 Moiety with Improved Potency", Bioorg. & Med. Chem. Let., vol. 15, (2005), pp. 4180-4184.
Avolio, S., "Inhibitors of hepatitis C virus NS3/4A: a-Ketoamide based macrocyclic inhibitors," Bioorganic & Medicinal Chemistry Letters (2009), 19, pp. 2295-2298.
Bastos, M., "Inhibitors of Human Heart Chymase Based on a Peptide Library", Proc. Natl. Acad. Sci. USA, vol. 92 (1995), pp. 6738-6742.
Beak, P., "Complex Induced Proximity Effects: Enantioselective Syntheses Based on Asymmetric Deprotonations of N-Boc-Pyrrolidines", J. Amer. Chem. Soc., vol. 116 (1994), pp. 3231-3239.
Behrens, C., "Selective Transformations of 2,3-Epoxy alcohols and Related Derivatives. Strategies for Nucleophilic Attack at Carbon-3 or Carbon-2", J. Org.Chem., vol. 50 (1985), pp. 5696-5704.

(Continued)

*Primary Examiner* — Rei-tsang Shiao
(74) *Attorney, Agent, or Firm* — Honigman Miller Schwartz and Cohn; Kathryn D. Soulier; Jonathan P. O'Brien

(57) ABSTRACT

The invention relates to co-crystals and compositions each comprising VX-950 and a co-crystal former selected from the group consisting of 3-methoxy-4-hydroxybenzoic acid, 2,4-dihydroxybenzoic acid, and 2,5-dihydroxybenzoic acid. Also within the scope of this invention are methods of making and using the same.

8 Claims, 9 Drawing Sheets

U.S. PATENT DOCUMENTS

| | | |
|---|---|---|
| 6,274,613 B1 | 8/2001 | Plant et al. |
| 6,303,287 B1 | 10/2001 | Kim et al. |
| 6,322,847 B1 | 11/2001 | Zhong et al. |
| 6,323,180 B1 | 11/2001 | Llinas-Brunet et al. |
| 6,329,417 B1 | 12/2001 | Llinas-Brunet et al. |
| 6,344,465 B1 | 2/2002 | Armistead et al. |
| 6,348,608 B1 | 2/2002 | Shi |
| 6,399,771 B1 | 6/2002 | Plant et al. |
| 6,410,531 B1 | 6/2002 | Llinas-Brunet et al. |
| 6,420,380 B2 | 7/2002 | Llinas-Brunet et al. |
| 6,420,522 B1 | 7/2002 | Bemis et al. |
| 6,498,178 B2 | 12/2002 | Stamos et al. |
| 6,528,276 B1 | 3/2003 | Germann et al. |
| 6,534,523 B1 | 3/2003 | Llinas-Brunet et al. |
| 6,541,496 B1 | 4/2003 | Armistead et al. |
| 6,548,555 B1 | 4/2003 | Curatolo et al. |
| 6,569,195 B2 | 5/2003 | Yang et al. |
| 6,608,027 B1 | 8/2003 | Tsantrizos et al. |
| 6,608,067 B1 | 8/2003 | Tung et al. |
| 6,617,309 B2 | 9/2003 | Tung et al. |
| 6,653,127 B1 | 11/2003 | Malcolm et al. |
| 6,653,295 B1 | 11/2003 | Glunz et al. |
| 6,699,855 B2 | 3/2004 | Zhang et al. |
| 6,727,366 B2 | 4/2004 | Han et al. |
| 6,767,991 B1 | 7/2004 | Llinas-Brunet et al. |
| 6,774,212 B2 | 8/2004 | Han |
| 6,800,434 B2 | 10/2004 | Saksena et al. |
| 6,824,769 B2 | 11/2004 | Chaturvedi et al. |
| 6,833,442 B2 | 12/2004 | Shibasaki et al. |
| 6,838,475 B2 | 1/2005 | Arasappan et al. |
| 6,846,802 B2 | 1/2005 | Chen et al. |
| 6,846,806 B2 | 1/2005 | Priestley |
| 6,867,284 B1 | 3/2005 | Matassa et al. |
| 6,872,805 B2 | 3/2005 | Campbell et al. |
| 6,909,000 B2 | 6/2005 | Farmer et al. |
| 6,911,428 B2 | 6/2005 | Zhu et al. |
| 6,914,122 B2 | 7/2005 | Venkatraman et al. |
| 6,919,423 B2 | 7/2005 | Llinas-Brunet et al. |
| 7,012,066 B2 | 3/2006 | Saksena et al. |
| 7,109,172 B2 | 9/2006 | Britt et al. |
| 7,244,721 B2 | 7/2007 | Saksena et al. |
| 7,273,885 B2 | 9/2007 | Pitlik et al. |
| 7,288,624 B2 | 10/2007 | Bemis et al. |
| 7,365,092 B2 | 4/2008 | Cottrell et al. |
| 7,371,372 B2 | 5/2008 | Chaturvedi et al. |
| 7,378,422 B2 | 5/2008 | Perni et al. |
| 7,381,827 B2 | 6/2008 | Tanoury et al. |
| 7,388,017 B2 | 6/2008 | Tung et al. |
| 7,504,378 B2 | 3/2009 | Llinas-Brunet et al. |
| 7,592,316 B2 | 9/2009 | Njoroge et al. |
| 7,820,671 B2 * | 10/2010 | Babine et al. ............ 514/252.1 |
| 2002/0016294 A1 | 2/2002 | Venkatraman et al. |
| 2002/0016442 A1 | 2/2002 | Llinas-Brunet et al. |
| 2002/0032175 A1 | 3/2002 | Tung et al. |
| 2002/0037998 A1 | 3/2002 | Llinas-Brunet et al. |
| 2002/0042046 A1 | 4/2002 | Kim et al. |
| 2002/0045729 A1 | 4/2002 | Kerres et al. |
| 2002/0065248 A1 | 5/2002 | Zhang et al. |
| 2002/0068702 A1 | 6/2002 | Lim-Wilby |
| 2002/0102235 A1 | 8/2002 | Arasappan et al. |
| 2002/0107181 A1 | 8/2002 | Chen et al. |
| 2002/0111378 A1 | 8/2002 | Stamos et al. |
| 2002/0123468 A1 | 9/2002 | Han |
| 2002/0142449 A1 | 10/2002 | Kwong et al. |
| 2002/0147160 A1 | 10/2002 | Bhat et al. |
| 2002/0160962 A1 | 10/2002 | Saksena et al. |
| 2002/0177725 A1 | 11/2002 | Priestley et al. |
| 2002/0183249 A1 | 12/2002 | Taylor et al. |
| 2002/0187488 A1 | 12/2002 | Lin et al. |
| 2003/0008828 A1 | 1/2003 | Priestley et al. |
| 2003/0036501 A1 | 2/2003 | Saksena et al. |
| 2003/0064962 A1 | 4/2003 | Glunz et al. |
| 2003/0068369 A1 | 4/2003 | McAllister et al. |
| 2003/0083467 A1 | 5/2003 | Germann et al. |
| 2003/0100768 A1 | 5/2003 | Han et al. |
| 2003/0119752 A1 | 6/2003 | Farmer et al. |
| 2003/0144257 A1 | 7/2003 | Biggadike et al. |
| 2003/0153788 A1 | 8/2003 | Kobayashi et al. |
| 2003/0181363 A1 | 9/2003 | Llinas-Brunet et al. |
| 2003/0186895 A1 | 10/2003 | Llinas-Brunet et al. |
| 2003/0186952 A1 | 10/2003 | Crew et al. |
| 2003/0187018 A1 | 10/2003 | Llinas-Brunet et al. |
| 2003/0191067 A1 | 10/2003 | Llinas-Brunet et al. |
| 2003/0195362 A1 | 10/2003 | Kempf et al. |
| 2003/0216325 A1 | 11/2003 | Saksena et al. |
| 2003/0236242 A1 | 12/2003 | Perni et al. |
| 2004/0006237 A1 | 1/2004 | Dolitzky et al. |
| 2004/0018986 A1 | 1/2004 | Pitlik et al. |
| 2004/0048774 A1 | 3/2004 | Saunders et al. |
| 2004/0058982 A1 | 3/2004 | Harris et al. |
| 2004/0067901 A1 | 4/2004 | Bhat et al. |
| 2004/0072788 A1 | 4/2004 | Bhat et al. |
| 2004/0077600 A1 | 4/2004 | Tung et al. |
| 2004/0082574 A1 | 4/2004 | Wang et al. |
| 2004/0105820 A1 | 6/2004 | Weers et al. |
| 2004/0110747 A1 | 6/2004 | Altman |
| 2004/0142876 A1 | 7/2004 | Colarusso et al. |
| 2004/0171626 A1 | 9/2004 | Beaulieu et al. |
| 2004/0180815 A1 | 9/2004 | Nakajima et al. |
| 2004/0186125 A1 | 9/2004 | Poupart et al. |
| 2004/0224900 A1 | 11/2004 | Bailey et al. |
| 2004/0229817 A1 | 11/2004 | Duggal et al. |
| 2004/0229818 A1 | 11/2004 | Llinas-Brunet |
| 2004/0266731 A1 | 12/2004 | Tung et al. |
| 2005/0020503 A1 | 1/2005 | Llinas-Brunet et al. |
| 2005/0136400 A1 | 6/2005 | Lin et al. |
| 2005/0137139 A1 | 6/2005 | Perni et al. |
| 2005/0153877 A1 | 7/2005 | Miao et al. |
| 2005/0187165 A1 | 8/2005 | Scola et al. |
| 2005/0187192 A1 | 8/2005 | Fleming et al. |
| 2005/0192212 A1 | 9/2005 | Llinas-Brunet et al. |
| 2005/0197299 A1 | 9/2005 | Babine et al. |
| 2005/0197301 A1 | 9/2005 | Njoroge et al. |
| 2005/0215486 A1 | 9/2005 | Cottrell et al. |
| 2005/0222236 A1 | 10/2005 | Tsantrizos et al. |
| 2005/0249702 A1 | 11/2005 | Njoroge et al. |
| 2005/0287514 A1 | 12/2005 | Byrn |
| 2006/0003317 A1 | 1/2006 | Perni et al. |
| 2006/0003942 A1 | 1/2006 | Tung et al. |
| 2006/0046956 A1 | 3/2006 | Sannigrahi et al. |
| 2006/0089385 A1 | 4/2006 | Cui et al. |
| 2006/0105978 A1 | 5/2006 | Chu et al. |
| 2006/0205672 A1 | 9/2006 | Saksena et al. |
| 2006/0211629 A1 | 9/2006 | Britt et al. |
| 2007/0087973 A1 | 4/2007 | Tanoury et al. |
| 2007/0105781 A1 | 5/2007 | Lyons et al. |
| 2007/0161789 A1 | 7/2007 | Cottrell et al. |
| 2007/0179167 A1 | 8/2007 | Cottrell et al. |
| 2007/0191381 A1 | 8/2007 | Tung et al. |
| 2007/0212683 A1 | 9/2007 | Connelly |
| 2007/0218012 A1 | 9/2007 | Bittorf et al. |
| 2007/0218138 A1 | 9/2007 | Bittorf et al. |
| 2007/0225297 A1 | 9/2007 | Perni et al. |
| 2007/0231262 A1 | 10/2007 | Lin et al. |
| 2007/0243166 A1 | 10/2007 | Llinas-Brunet et al. |
| 2007/0244334 A1 | 10/2007 | Tanoury et al. |
| 2007/0292933 A1 | 12/2007 | Pitlik et al. |
| 2008/0045480 A1 | 2/2008 | Farmer et al. |
| 2008/0070972 A1 | 3/2008 | Kadiyala et al. |
| 2008/0125376 A1 | 5/2008 | Cottrell et al. |
| 2008/0167480 A1 | 7/2008 | Wallace |
| 2008/0267915 A1 | 10/2008 | Lin et al. |
| 2008/0311079 A1 | 12/2008 | Perni et al. |
| 2009/0022688 A1 | 1/2009 | Farmer et al. |
| 2009/0143312 A1 | 6/2009 | Tung et al. |
| 2009/0191555 A1 | 7/2009 | Lin et al. |
| 2009/0247468 A1 | 10/2009 | Bittorf et al. |

FOREIGN PATENT DOCUMENTS

| | | |
|---|---|---|
| EP | 0675112 | 10/1995 |
| JP | 09124691 | 5/1997 |
| WO | WO 92/12140 | 7/1992 |
| WO | WO 93/25574 | 12/1993 |
| WO | WO 94/14436 | 7/1994 |
| WO | WO 95/07696 | 3/1995 |
| WO | WO 95/09614 | 4/1995 |
| WO | WO 96/011697 | 4/1996 |

| | | |
|---|---|---|
| WO | WO 97/17364 | 5/1997 |
| WO | WO 97/40028 | 10/1997 |
| WO | WO 97/43310 | 11/1997 |
| WO | WO 98/13365 | 4/1998 |
| WO | WO 98/17679 | 4/1998 |
| WO | WO 98/22496 | 5/1998 |
| WO | WO 98/40381 | 9/1998 |
| WO | WO 98/46630 | 10/1998 |
| WO | WO 99/07733 | 2/1999 |
| WO | WO 99/07734 | 2/1999 |
| WO | WO 99/38888 | 8/1999 |
| WO | WO 99/50230 | 10/1999 |
| WO | WO 99/64442 | 12/1999 |
| WO | WO 00/09543 | 2/2000 |
| WO | WO 00/09558 | 2/2000 |
| WO | WO 00/09588 | 2/2000 |
| WO | WO 00/23421 | 4/2000 |
| WO | WO 00/31129 | 6/2000 |
| WO | WO 00/56331 | 9/2000 |
| WO | WO 00/59929 | 10/2000 |
| WO | WO 01/02424 | 1/2001 |
| WO | WO 01/07407 | 2/2001 |
| WO | WO 01/32691 | 5/2001 |
| WO | WO 01/40262 | 6/2001 |
| WO | WO 01/40266 | 6/2001 |
| WO | WO 01/58929 | 8/2001 |
| WO | WO 01/64678 | 9/2001 |
| WO | WO 01/74768 | 10/2001 |
| WO | WO 01/77113 | 10/2001 |
| WO | WO 01/81325 | 11/2001 |
| WO | WO 02/07761 | 1/2002 |
| WO | WO 02/08187 | 1/2002 |
| WO | WO 02/08198 | 1/2002 |
| WO | WO 02/08244 | 1/2002 |
| WO | WO 02/08251 | 1/2002 |
| WO | WO 02/08256 | 1/2002 |
| WO | WO 02/18369 | 3/2002 |
| WO | WO 02/48116 | 6/2002 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/074474 | 9/2003 |
| WO | WO 03/087092 | 10/2003 |
| WO | WO 2004/026896 | 4/2004 |
| WO | WO 2004/030670 | 4/2004 |
| WO | WO 2004/032827 | 4/2004 |
| WO | WO 2004/037855 | 5/2004 |
| WO | WO 2004/039833 | 5/2004 |
| WO | WO 2004/064762 | 8/2004 |
| WO | WO 2004/072243 | 8/2004 |
| WO | WO 2004/078161 | 9/2004 |
| WO | WO 2004/089974 | 10/2004 |
| WO | WO 2004/092161 | 10/2004 |
| WO | WO 2004/093798 | 11/2004 |
| WO | WO 2004/094452 | 11/2004 |
| WO | WO 2004/103996 | 12/2004 |
| WO | WO 2004/113365 | 12/2004 |
| WO | WO 2005/007681 | 1/2005 |
| WO | WO 2005/010029 | 2/2005 |
| WO | WO 2005/021584 | 3/2005 |
| WO | WO 2005/028501 | 3/2005 |
| WO | WO 2005/028502 | 3/2005 |
| WO | WO 2005/030796 | 4/2005 |
| WO | WO 2005/035525 | 4/2005 |
| WO | WO 2005/037214 | 4/2005 |
| WO | WO 2005/037860 | 4/2005 |
| WO | WO 2005/042570 | 5/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/058821 | 6/2005 |
| WO | WO 2005/070955 | 8/2005 |
| WO | WO 2005/073195 | 8/2005 |
| WO | WO 2005/073216 | 8/2005 |
| WO | WO 2005/077969 | 8/2005 |
| WO | WO 2005/085242 | 9/2005 |
| WO | WO 2005/085275 | 9/2005 |
| WO | WO 2005/087721 | 9/2005 |
| WO | WO 2005/087725 | 9/2005 |
| WO | WO 2005/087731 | 9/2005 |
| WO | WO 2005/095403 | 10/2005 |
| WO | WO 2005 107745 | 11/2005 |
| WO | WO 2005/113581 | 12/2005 |
| WO | WO 2005/120393 | 12/2005 |
| WO | WO 2005/123076 | 12/2005 |
| WO | WO 2006/000085 | 1/2006 |
| WO | WO 2006/007448 | 1/2006 |
| WO | WO 2006/007700 | 1/2006 |
| WO | WO 2006/007708 | 1/2006 |
| WO | WO 2006/050250 | 5/2006 |
| WO | WO 2006/124823 | 11/2006 |
| WO | WO 2007/016589 | 2/2007 |
| WO | WO 2007/025307 | 3/2007 |
| WO | WO 2007/030478 | 3/2007 |
| WO | WO 2007/098270 | 8/2007 |
| WO | WO 2007/128969 | 11/2007 |
| WO | WO 2007/140320 | 12/2007 |
| WO | WO 2008/027871 | 3/2008 |
| WO | WO 2008/027872 | 3/2008 |
| WO | WO 2008/098255 | 8/2008 |
| WO | WO 2008/106058 | 9/2008 |

OTHER PUBLICATIONS

Bergmeier, S.C., "Synthesis of Bicyclic Proline Analogs Using a formal [3+2] Intramol ecular Aziridine-Allylsilane Cycloaddition Reaction", Tetrahedron, vol. 55, No. 26 (1999), pp. 8025-8038.

Blair, W., "5th Antiviral Drug Discovery and Development Summit," Expert opinion on investigational drugs (2004), 13 (8), pp. 1065-1069.

Blankley, C.J., "Synthesis and Structure-Activity Relationships of Potent New Abgiotensin Converting Enzyme Inhibitors Containing Saturated Bicyclic Amino Acids", J. of Medicinal Chem., vol. 30 (1987).

Cacciola, J., "The Synthesis of Lysine a-Ketoamide Thrombin Inhibitors via an Epoxy Amide Ring Opening", Tetrahedron Let., vol. 38, No. 33 (1977), pp. 5741-5744.

Chawla, et al., "Challenges in Polymorphism of Pharmaceuticals", CRIPS vol. 5, No. 1, Jan.-Mar. 2004, pp. 9-12.

Chen, S., "Synthesis and Evaluation of Tripeptidyl a-Ketoamides as Human Rhinovirus 3C Protease Inhibitors", Bioorg. & Med. Chem. Letters, vol. 13, No. 20 (2003), pp. 3531-3536.

Chen, S., "Discovery of Small-Molecule Inhibitors of HCV NS3-4A Protease as Potential Therapeutic Agents against HCV Infection," Current Medicinal Chemistry (2005), 12(20), pp. 2317-2342.

Chen, S., "P1 and P1' Optimization of [3,4]-Bicycloproline P2 Incorporated Tetrapeptidyl a-ketoamide Based HCV Protease Inhibitors," Letters in Drug Design and Discovery (2005), 2(2), pp. 118-123.

Cheng, W., "Stereoselective Synthesis of Unnatural Spiroisoxazolinoproline-Based Acids and Derivatives", J. Org. Chem., (2002), pp. 5673-5677.

Collado, I., "Stereocontrolled Synthesis of 4-Substituted (±)-Kainic Acids", Journal of Organic Chem., vol. 63 (1998).

Davis, G. "Future Options for the Management of Hepatitis C", Seminars in Liver Disease, vol. 19, Supp. 1 (1999), pp. 103-112.

Dixon, S. M., "A Spiroisoazolinoproline-based Amino Acid Scaffold for Solid Phase and One-Bead—One-Compound Library Synthesis" Journal of Combinatorial Chemistry, 9 (2007) pp. 143-157.

Dunsdon, R., "Solid Phase Synthesis of Aminoboronic Acids: Potent Inhibitors of the Hepatitis C Virus NS3 Proteinase", Bioorganic & Medicinal Chemistry Letters, 10 (2000), pp. 1577-1579.

Elemes, "Synthesis of enantiopure a-deuterated Boc-L amino acids," J. Chemical Society, Perkin Trans. vol. 1 (1995) pp. 537-540.

Esch, P.M., "Reductive Cyclization of Carbon-Centered Glycine Radicals; A Novel Synthetic route to Cyclic a-Amino Acids", Tetrahedron, vol. 48, No. 22 (1992), pp. 4659-4676.

Farmer, L., "Inhibitors of Hepatitis C Virus NS3-4A Protease: P2 Proline Variants," Letters in Drug Design and Discovery (2005), 2, pp. 497-502.

Forestier, Current status of subjects receiving peg-interferon-alfa-2a (PEG-IFN) and ribavirin (RBV) after a 14-day study of the hepatitis C protease inhibitor telaprevir (VX-950), with PEG-IFN, Hepatology, vol. 44, Supp. 2 (2006), p. 614A.

Freireich, E., "Quantitative Comparison of Toxicity of Anticancer Agents in Mouse, Rat, Hamster, Dog, Monkey and Man", Cancer Chemother. Rep., vol. 50 No. 219 (1966), pp. 219-244.

Gallagher, D., "Complex-Induced Proximity Effects: Evidence for a Prelithiation Complex and a Rate-Determining Deprotonation in the Asymmetric Lithiation of Boc-Pyrrolidine by an i-PrLi/(−) Sparteine Complex", J. Org. Chem., vol. 60 (1995), pp. 7092-7093.

Gallagher, D., "Chiral Organolithium Complexes: The Effect of Ligand Structure on the Enantioselective Deprotonation of Boc-Pyrrolidine", J. Org. Chem., vol. 60 (1995), pp. 8148-8154.

Garrison, G., "Novel 3,7-Diheterabicyclo[3.3.1]nonanes that Possess Predominant Class III Antiarrhythmic Activity in 1-4 Day Post Infarction Dog Models: X-ray Diffraction Analysis of 3-[4-(1 H-Imidazol-1-yl)benzoyl]-7-isopropyl-3,7-diazabicyclo[3.3. 1]nonane Dihydroperchlorate", J. Med. Chem, vol. 39, No. 13 (1996), pp. 2559-2570.

Golina, S., "Vulcanisation of Poly(diethyl-n-butylamino) Phosphazenes", Internat'l. Polymer Science & Tech., vol. 18, No. 3 (1991), pp. T20-T22.

Han, W., "a-Ketoamides, a-Ketoesters and a-Diketones as HCV NS3 Protease Inhibitors", Bioorganic & Medicinal Chemistry Letters 10 (2000), pp. 711-713.

Hofma, S.H. "Recent developments in Coated Stents," Curr. Interventional Cardiology Reports, 3 (2001), pp. 28-36.

Janssen, H.L.A., "Suicide Associated with a-Interferon Therapy for Chronic Viral Hepatitis", J. Hepatol., 21 (1994), pp. 241-243.

Johansson, A., "Acyl Sulfonamides as Potent Protease Inhibitors of the Hepatitis C Virus Full-Length NS3 (Protease-Helicase/NTPase): A comparative Study of Different C-Terminals", Bioorganic & Medicinal Chemistry, 11 (2003), pp. 2551-2568.

Johansson, P., "Potent inhibitors of the hepatitis C virus NS3 protease: Use of a novel P2 cyclopentane-derived template," Bioorganic & Medicinal Chemistry (2006), 14, pp. 5136-5151.

Kakei, H., "Catalytic Asymmetric Epoxidation of a, β-Unsaturated Esters Using an Yttrium-Biphenyldiol Complex", J. Am. Chem. Soc., vol. 127 (2005), pp. 8962-8963.

Kalkeri, G., "Expression of HCV Protease in the Liver of Mice Results in Liver Injury Which can be Inhibited by VX-950, A Vertex HCV Protease Inhibitor," AALSD Abstracts, Hepatology (2004), 40(4), pp. 281A.

Kamandi, E., "Die Synthese von β-Phenyl-Isoserinen Durch Ammonolyse von β-Phenyl-Glycidestern, I", Archiv de Pharmazie, vol. 307 No. 11 (1974), pp. 871-878.

Kao, J.H., "Efficacy of Consensus Interferon in the Treatment of Chronic Hepatitis", J. Gastroenterol. Hepatol, 15 (2000), pp. 1418-1423.

Kerrick, S., "Asymmetric Deprotonations: Enantioselective Syntheses of 2-Substituted (tert-Butoxycarbonyl) pyrrolldines", J. Amer. Chem. Soc., vol. 113 (1991), pp. 9708-9710.

Kieffer, T., "Genetic Heterogeneity in the HCV NS3 Protease of Untreated Genotype 1 Patients has Little Effect on the Sensitivity to VX-950", Hepatol, vol. 42 (2005), p. 537A.

Kieffer, T., "Wild-Type HCV NS3 Protease Re-Emerges During Follow-up After 14 days of Dosing with VX-950 in Patients with Genotype 1 HCV", J. Hepatol, vol. 44 Supp. 2 (2006), p. S7.

Kieffer, T., "Combination of Telaprevir (VX-950) and Peg-Ifn-Alfa Suppresses both Wild-Type Virus and Resistance Variants in HCV Genotype 1-Infected Patients in a 14-Day Phase 1B Study", Hepatol. 44, Supp.2 (2006), p. 222A.

Kieffer, Genetic Heterogeneity in the HCV Ns3 Protease of Untreated Genotype 1 Patients Has Little Effect on the Sensitivity of the VX-950, 12th Internat'l. Conf. on Hep. C Virus and Related Viruses, Montreal, Canada, Oct. 2-6, 2005.

Kim, J., "Hepatitis C Virus NS3 RNA Helicase Domain with a bound Oligonucleotide: The Crystal Structure Provides Insights into the Mode of Unwinding", Structure, vol. 6, No. 1, (1998), pp. 89-100.

Kim, J., "Crystal structure of the hepatitis C virus NS3 protease domain complexed with a synthetic NS4A cofactor peptide," Cell, vol. 87 (1996), pp. 343-355; [and Kim, J. "Erratum," Cell, vol. 89, No. 1 (1997), p. 159].

Kino, R., "Remarkable Effect of tris(4-fluorphenyl)phosphine Oxide on the Stabilization of Chiral Lanthanum Complex Catalysis. A New and Practical Protocol for the Highly Enantioselective Epoxidation of Conjugated Enones", Org. Biomol. Chem., vol. 2 (2004), pp. 1822-1824.

Kwong, A.D., "Structure and Function of Hepatitis C Virus NS3 Helicase", Top Microbiol. Immunol., vol. 242, (2000), pp. 171-196.

Kwong, A.D., "Hepatitis C Virus NS3/4A Protease", Antiviral Res., vol. 40 (1998), pp. 1-18.

Kwong, A.D., "Erratum: Hepatitis C Virus NS3/4A Protease", Antiviral Res., vol. 41 (1999), pp. 65-84.

Kwong, A.D., "An Orally Bioavailable Inhibitor of the HCV NS3-4a Protease; a Potential HCV Therapeutic", 5th Antivir. Drug Disc. and Devel. Summit, (Mar. 30, 2004).

Kwong, A.D., "HCV Protease Inhibitors: Activity and Resistance," 13th Conference on Retroviruses and Opp. Infections (CROI), Denver, CO, Feb. 5-8, 2006.

Kwong, A.D., "Beyond Interferon and Ribavirin: Antiviral Therapies for Hepatitis C Virus", Drug Disc. Today: Ther. Strategies, vol. 3 (2006), pp. 211-220.

Kwong, A.D., "VX-950: A Novel Hepatitis C Protease Inhibitor", HepDART (2005).

Lamar, J., "Novel P4 Truncated Tripeptidyl a-ketoamides as HCV Protease Inhibitors", Bio. & Med. Chem. Let, vol. 14 No. 1 (2004), pp. 263-266.

Landro, J.A. "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 36 (1997) pp. 9340-9348.

Laplante, S., "NMR Line-Broadening and Transferred NOESY as a Medicinal Chemistry Tool for Studying Inhibitors of the Hepatitis C Virus NS3 Protease Domain", Bioorganic & Medicinal Chemistry Letters, 10 (2000), pp. 2271-2274.

Lavanchy, D., "Global Surveillance and control of Hepatitis C", J. Viral Hepatitis, 6 (1999), pp. 35-47 .

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", 12th Internat'l Symposium on Viral Hep. and Liver Dis., (2006).

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", Gastroenterol. vol. 131(3) (2006) pp. 950-951.

Lehmann, Über die chemischen and biologischen Eigenschaften einiger a-Aminoketone, Helvetica Chimica Acta., vol. 33 (1950), pp. 1217-1226.

Lin, C., "Structure-Based Mutagenesis Study of Hepatitis C Virus NS3 Helicase", J. Virol., vol. 73, No. 10 (1999), pp. 8798-8807.

Lin, K., "Combination of a Hepatitis C Virus NS3-NS4A Protease Inhibitor and a Interferon Synergistically Inhibits Viral RNA Replication and Facilitates Viral RNA Clearance in Replicon Cells", Antimicrob. Agents Chemo, vol. 48 (2004), pp. 4784-4792.

Lin, K., "VX-950, a Novel Hepatitis C Virus (HCV) NS3-4A Protease Inhibitor, Exhibits Potent Antiviral Activities in HCV Replicon Cells", Antimicrob. Agents Chemo, vol. 50, No. 5 (2006), pp. 1813-1822.

Lin, K., "VX-950: A Tight-Binding HCV Protease Inhibitor with a Superior Sustained Inhibitory Response in HCV Replicon Cells", Hepatol, vol. 38 (2003), p. 222A.

Lin, C., "Discovery and Development of VX-950, a Novel, Covalent and Reversible Inhibitor of Hepatitis C Virus NS3-4A Serine Protease", Infect. Disord. Drug Targets, vol. 6, No. 1 (2006), pp. 3-16.

Lin, C., "In Vitro Resistance Studies of Hepatitis C Virus Serine Protease Inhibitors, VX-950 and BILN 2061", J. Biol. Chem., vol. 279, No. 17 (2004), pp. 17508-17514.

Llinas-Brunet, M., "Highly Potent and Selective Peptide-Based Inhibitors of the Hepatitis C Virus Serine Protease: Towards Smaller Inhibitors", Bioorganic & Medicinal Chemistry Letters, 10 (2000), pp. 2267-2270.

Llinas-Brunet, M., "Peptide-Based Inhibitors of the Hepatitis C Virus Serine Protease", Bioorganic & Medicinal Chemistry Letters, 8 (1998), pp. 1713-1718.

Llinas-Brunet, M., "Studies on the C-Terminal of Hexapeptide Inhibitors of the Hepatitis C virus Serine Protease", Bioorganic & Medicinal Chemistry Letters, 8 (1998), pp. 2719-2724.

Lohmann, F. "Replication of Subgenomic Hepatitis C Virus RNAs in a Hepatoma Cell Line", Science, 285.5454 (1999) p. 110.

Marigo, M., "Asymmetric Organocatalytic Epoxidation of a,β-Unsaturated Aldehydes with Hydrogen Peroxide", J. Am. Chem. Soc., vol. 127, No. 19 (2005), pp. 6964-6965.

Markland, W., "Broad-Spectrum Antiviral Activity of the IMP Dehydrogenase Inhibitor VX-497: a Comparison with Ribavirin and Demonstration of Antiviral Additivity with Alpha Interferon", Antimicrob. Ag. Chem., vol. 44, No. 4 (2000), pp. 859-866.

McLaren, R., "Infrared Observations of Circumstellar Ammonia in OH/IR Supergiants," Astrophysical Journal (1980), 240(3, Pt. 2), pp. L159-L163.

Mehdi, The Inhibition of Human Neutrophil Elastase and Cathepsin G by Peptidyl 1,2-Dicarbonyl Derivatives, Biochem & Biophys. Res. Comm., vol. 166, No. 2 (1990), pp. 595-660.

Monn, J., "A Concise, Stereocontrolled Thiazolium Ylide Approach to Kainic Acid", J. Organic Chem., vol. 59, No. 10 (1994), pp. 2773-2778.

Moradpour, D., "Current and Evolving Therapies for Hepatitis C", Eur. J. Gastroenterol. Hepatol., vol. 11 (1999), pp. 1199-1202.

Morgenstern, J., "Polynucleotide Modulation of the Protease, Nucleoside Triphosphatase, and Helicase Activities of a Hepatitis C Virus NS3-NS4A Complex Isolated from Transfected COS Cells", J. Virol., vol. 71, No. 5 (1997), pp. 3767-3775.

Newman, A., "Solid-state Analysis of the Active Pharmaceutical Ingredient in Drug Products", vol. 8, No. 19 (2003), pp. 898-905.

Patent Abstracts of Japan, vol. 1997, No. 9, Sep. 30, 1997.

Perni, R., "NS3-4A Protease as a Target for Interfering with Hepatitis C Virus Replication", Drug News Perspect., vol. 13, No. 2 (2000), pp. 69-77.

Perni, R.B., "Inhibitors of Hepatitis C Virus NS3-4A Protease 1. Non-Charged Tetrapeptide Variants", Bioorganic & Medicinal Chemistry Letters, 13 (2003), pp. 4059-4063.

Perni, R.B., "Inhibitors of Hepatitis C Virus NS3-4A Protease 2. Warhead SAR and Optimization", Bioorganic & Medicinal Chemistry Letters, 14 (2004), pp. 1441-1446.

Perni, R.B., "Inhibitors of Hepatitis C Virus NS3-4A Part 3: P2 Proline Variants", Bioorganic & Medicinal Chemistry Letters, 14 (2004), pp. 1939-1942.

Perni, Preclinical Profile of VX-950, a Potent, Selective, and Orally Bioavailable Inhibitor of Hepatitis C Virus N53-4A Serine Protease, Antimicrob. Agents Chemo., vol. 50, No. 3, Mar. 2006, pp. 899-909.

Perni, R. "VX-950: The Discovery of an Inhibitor of the Hepatitis C NS3-4A Protease and a Potential Hepatitis C Virus Therapeutic", Hepatology, vol. 38 (2003) p. 624A.

Perni, R., "Toward Smaller HCV NW-4A Protease Inhibitors: 3-Substituted Proline-based Tripeptide Scaffolds," Abstracts of Papers, 229th ACS National Meeting, San Diego, CA, United States, Mar. 13-17, 2005, MEDI-350.

Perni, R., "The Design of Inhibitors of the HCV NS3-4A Protease: The Identification of a Clinical Development Candidate, VX-950," ACS National Medicinal Chemistry Symposium, Madison, WI, Jun. 2004.

Perni, R., "Inhibitors of Hepatitis C Virus NS3-4A Protease. Effect of P4 Capping Groups on Inhibitory Potency and Pharmacokinetics," Bioorganic & Medicinal Chemistry Letters (2007), 17(12), pp. 3406-3411.

Perni, R., "Properties and Preclinical Profile of VX-950, An Orally Bioavailable Inhibitor of the Hepatitis C Virus (HCV) Protease and a Potential Anti-HCV Therapeutic," 10th International Symposium on Hepatitis C and Related Viruses, Kyoto, Japan, Dec. 2-6, 2003.

Perni, R., "The Importance of Backbone Hydrogen Bonds in Binding a Tetrapeptide Scaffold to the HCV NS3-4A Protease," American Chemical Society's 229th National Meeting, San Diego, CA, Mar. 13-17, 2005.

Pippel, D., "Complex-Induced Proximity Effects: Steroselective Carbon-Carbon Bond Formation in Chiral Auxiliary Mediated β-Lithiation-Substitution Sequences of β-Substituted Secondary Carboxamides", J. Org. Chem., vol. 63 (1998), pp. 2-3.

Poliakov, A. "Structure-Activity Relationships for the Selectivity of Hepatitis C Virus NS3 Protease Inhibitors", Biochimica et Biophysica Acta, 1672 (2004), pp. 51-59.

Ramachandran, R., "Anti-Viral Activity of VX-950 Resolves Expression of an HCV-Associated Gene Signature", J. Hepatol, vol. 44, Supp. 2 (2006), p. S223.

Reesink, H., "Initial Results of a Phase 1B, Multiple-Dose Study of VX-950, a Hepatitis C Virus Protease Inhibitor", Gastroent., vol. 128, No. 4, Supp. 2 (2005), pp. A696-A697.

Reesink, H., "Rapid Decline of Viral RNA in Hepatitis C Patients Treated with VX-950: A Phase 1b, Placebo-Controlled Randomized Study", Gastroenterol., vol. 131, No. 4 (2006), pp. 997-1002.

Reesink, H., "Final Results of a Phase 1B, Multiple-Dose Study of VX-950, a Hepatitis C Virus Protease Inhibitor", Hepatology, vol. 42, No. 4, Supp. 1 (2005), pp. 234A-235A.

Reesink, H., "Initial Results of a 14-Day Study of the Hepatitis C Virus Inhibitor Protease VX-950, in combination with Peginterferon-Alpha-2a", J. Hepatol., vol. 44, Supp. 2 (2006), p. S272.

Renault, P.F., "Side Effects of Alpha Interferon", Seminars in Liver Disease, vol. 9 (1989), pp. 273-277.

Rodriguez-Torres, M., "Current Status of Subjects Receiving Peg-Interferon-Alfa-2A (PEG-IFN) and Ribavirin (RBV) Follow-on Therapy After 28-Day Treatment with the Hepatitis C Protease Inhibitor Telaprevir (VX-950), PEG-IFN and RBV", Hepatol., vol. 44, Supp. 2 (2006), p. 532A.

Sagnard, I, "Enantioselective Synthesis of Cyclopropane a-Amino Acids: Synthesis of N-Box-cis-(2S,3R,4S)-3,4-Methanoproline and N-Boc-(2S,3R,4S)-3,4-Methanoglutamic Acid", Tetrahedron, vol. 36, No. 18 (1995), pp. 3149-3152.

Schneider, F. "Enhanced Plasma Concentration by Selective Deuteration of Rofecoxib in Rats," Arzneimittel-Forschung (Drug. Res.) vol. 56 (4) (2006), pp. 295-300.

Schneider, F. "Changed Phosphodiestarase Selectivity and Enhanced in vitro Efficacy by Selective Deuteraton of Sildenafil," Arzneimittel-Forschung (Drug. Res.) vol. 57 (6) (2007), pp. 293-298.

Taber, D., "Asymmetric Nucleophilic Epoxidation", Org. Chem. Highlights, (2004).

Takamizawa, A., "Structure and Organization of the Hepatitis C Virus Genome Isolated from Human Carriers", J. Virol., 65 (1991), pp. 1105-1113.

Taliani, M., "A continuous Assay of Hepatitis C Virus Protease Based on Resonance Energy Transfer Depsipeptide Substrates", Anal. Biochem., vol. 240 (1996), pp. 60-67.

Tan, S., "Strategies for Hepatitis C Therapeutic Intervention: Now and Next", Current Op. in Pharmacology, vol. 4, No. 5 (2004), pp. 465-470.

Tazulakhova, E.B., "Russian Experience in Screening, Analysis and Clinical Application of Novel Interferon Inducers", J. Interferon Cytokine Res., 21 (2001), pp. 65-73.

Thomson, J., "Hepatitis C Virus NS3-4A Protease Inhibitors: countering Viral Subversion in vitro and Showing Promise in the Clinic", Curr. Opin. Drug Discov. Devel., vol. 9, No. 5 (2006), pp. 606-617.

Toom, L., "Microwave-Assisted Raney Nickel Reduction of Bispidinone Thioketals to N,N'-Dialkylbispidines", Synthesis, vol. 12 (2006), pp. 2064-2068.

Trask, A.V., "Solvent-drop grinding: green polymorph control of cocrystallisation", Chemical Communications, (2004), pp. 890-891.

Udding, J.H., "Transition Metal-Catalyzed Chlorine Transfer Cyclizations of Carbon-Centered Glycine Radicals; A Novel Synthetic Route to Cyclic a-Amino Acids", Tetrahedron, vol. 50, No. 6 (1994), pp. 1907-1918.

Victor, F., "P1 and P3 optimization of novel bicyproline P2 bearing tetrapeptidyl a-ketoamide based HCV protease inhibitors", Biorganic & Medicinal Chemistry Letters, 14 (2004), pp. 257-261.

Vishweshwar, P., "Pharmaceutical Co-Crystals", J. Pharm. Sci., vol. 95, No. 3 (2006), pp. 499-516.

Walker, M.A., "Hepatitis C Virus: An Overview of Current Approaches and Progress", DDT, 4 (1999), pp. 518-529.

Wang, Z., "Asymmetric Epoxidation of trans-β-Methylstyrene and 1-Phenylcyclohexene Using a D-Fructose-Derived Ketone: (R,R)-trans-β-Methylstyrene Oxide and (R,R)-1-Phenylcyclohexene Oxide", Org. Syntheses, vol. 80 (2003), pp. 9-13.

Weiland, O., "Interferon Therapy in Chronic Hepatitis C Virus Infection", FEMS Microiol. Rev., 14 (1994), pp. 279-288.

Weissbuch, I. et al. "Understanding and control of nucleation, growth, habit, dissolution and structure of two- and three-dimensional crystals using 'tailor-made' auxiliaries," Acta Crystallographica B vol. B51 (1995), pp. 115-148.

White, P.W. "Blunting the Swiss Army Knife of Hepatitis C Virus: Inhibitors of NS3/4A Protease", Progress in Medicinal Chemistry 44 (2006), pp. 65-107.

Yao, N. N. "Molecular views of viral polyprotein processing revealed by the crystal structure of the hepatitis C virus bifunctional protease-helicase," Structure (1999), 7, pp. 1353-1363.

Yasuda, M., "Synthesis of Conformationally Defined Glutamic Acid Analogues from Readily Available Diels-Alder Adducts", Chem. and Pharm. Bulletin (1995), pp. 1318-1324.

Yip, Y. Discovery of a Novel Bicycloproline P2 Bearing Peptidyl a-Ketoamide LY514962 as HCV Protease Inhibitor, Bio. & Med. Chem. Let., vol. 14, No. 1 (2004), pp. 251-256.

Yip, Y., "P4 and P1' Optimization of Bicycloproline P2 Bearing Tetrapeptidyl a-Ketoamides as HCV Protease Inhibitors", Bio. & Med. Chem. Let., vol. 14, No. 9 (2004), pp. 5007-5011.

Yun, C. "Oxidation of the antihistaminic drug terfenadine in human liver microsomes: Role of Cytochrome P-450 3A(4) in N-dealkylation and C-hydroxylation", Drug metabolism and Disposition, 21(3) (1993) pp. 403-409.

ISR dated Jul. 23, 2007 from PCT/US2007/006320.
ISR dated Aug. 3, 2007 from PCT/US2007/004995.
ISR dated Nov. 16, 2007 from PCT/US2007/64294.
ISR dated Dec. 27, 2007 from PCT/US2006/032481.
ISR dated Sep. 5, 2008 from PCT/US2008/002568.
ISR dated Jan. 21, 2009 from PCT/US2008/010254.
ISR dated Jan. 23, 2009 from PCT/US2008/002395.

* cited by examiner

CO-CRYSTALS AND PHARMACEUTICAL COMPOSITIONS COMPRISING THE SAME

CROSS REFERENCE

This application is a national phase entry of PCT/US2008/010254, filed Aug. 29, 2008, which claims the benefit of U.S. Provisional Application No. 60/969,023, filed Aug. 30, 2007. Both of these documents are incorporated herein in their entirety.

BACKGROUND OF THE INVENTION

Infection by hepatitis C virus ("HCV") is a compelling human medical problem. HCV is recognized as the causative agent for most cases of non-A, non-B hepatitis, with an estimated human prevalence of 3% globally [A. Alberti et al., "Natural History of Hepatitis C," *J. Hepatology*, 31 (Suppl. 1), pp. 17-24 (1999)]. Nearly four million individuals may be infected in the United States alone [M. J. Alter et al., "The Epidemiology of Viral Hepatitis in the United States, *Gastroenterol. Clin. North Am.*, 23, pp. 437-455 (1994); M. J. Alter "Hepatitis C Virus Infection in the United States," *J. Hepatology*, 31 (Suppl. 1), pp. 88-91 (1999)].

Upon first exposure to HCV, only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," *FEMS Microbiology Reviews*, 14, pp. 201-204 (1994); D. Lavanchy, "Global Surveillance and Control of Hepatitis C," *J. Viral Hepatitis*, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", *FEMS Microbiology Reviews*, 14, pp. 211-220 (1994); I. Saito et al., "Hepatitis C Virus Infection is Associated with the Development of Hepatocellular Carcinoma," *Proc. Natl. Acad. Sci. USA*, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et al., "Genetic Organization and Diversity of the Hepatitis C Virus," *Proc. Natl. Acad. Sci. USA*, 88, pp. 2451-2455 (1991); N. Kato et al., "Molecular Cloning of the Human Hepatitis C Virus Genome From Japanese Patients with Non-A, Non-B Hepatitis," *Proc. Natl. Acad. Sci. USA*, 87, pp. 9524-9528 (1990); A. Takamizawa et al., "Structure and Organization of the Hepatitis C Virus Genome Isolated From Human Carriers," *J. Virol.*, 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et al., "Nonstructural Protein 3 of the Hepatitis C Virus Encodes a Serine-Type Proteinase Required for Cleavage at the NS3/4 and NS4/5 Junctions," *J. Virol.*, 67, pp. 3835-3844 (1993); A. Grakoui et al., "Characterization of the Hepatitis C Virus-Encoded Serine Proteinase: Determination of Proteinase-Dependent Polyprotein Cleavage Sites," *J. Virol.*, 67, pp. 2832-2843 (1993); A. Grakoui et al., "Expression and Identification of Hepatitis C Virus Polyprotein Cleavage Products," *J. Virol.*, 67, pp. 1385-1395 (1993); L. Tomei et al., "NS3 is a serine protease required for processing of hepatitis C virus polyprotein", *J. Virol.*, 67, pp. 4017-4026 (1993)].

The HCV NS protein 3 (NS3) is essential for viral replication and infectivity [Kolykhalov, *J. Virology*, Volume 74, pp. 2046-2051 2000 "Mutations at the HCV NS3 Serine Protease Catalytic Triad abolish infectivity of HCV RNA in Chimpanzees]. It is known that mutations in the yellow fever virus NS3 protease decrease viral infectivity [Chambers, T. J. et al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.*, 68, pp. 8147-8157 (1994)].

The HCV NS3 serine protease and its associated cofactor, NS4A, help process all of the viral enzymes, and are thus considered essential for viral replication. his processing appears to be analogous to that carried out by the human immunodeficiency virus aspartyl protease, which is also involved in viral enzyme processing. HIV protease inhibitors, which inhibit viral protein processing, are potent antiviral agents in man indicating that interrupting this stage of the viral life cycle results in therapeutically active agents. Consequently, HCV NS3 serine protease is also an attractive target for drug discovery.

Until recently, the only established therapy for HCV disease was interferon treatment. However, interferons have significant side effects [M. A. Wlaker et al., "Hepatitis C Virus: An Overview of Current Approaches and Progress," *DDT*, 4, pp. 518-29 (1999); D. Moradpour et al., "Current and Evolving Therapies for Hepatitis C," *Eur. J. Gastroenterol. Hepatol.*, 11, pp. 1199-1202 (1999); H. L. A. Janssen et al. "Suicide Associated with Alfa-Interferon Therapy for Chronic Viral Hepatitis," *J. Hepatol.*, 21, pp. 241-243 (1994); P. F. Renault et al., "Side Effects of Alpha Interferon," *Seminars in Liver Disease*, 9, pp. 273-277 (1989)] and induce long term remission in only a fraction (~25%) of cases [O. Weiland, "Interferon Therapy in Chronic Hepatitis C Virus Infection", *FEMS Microbiol. Rev.*, 14, pp. 279-288 (1994)]. Recent introductions of the pegylated forms of interferon (PEG-INTRON® and PEGASYS®) and the combination therapy of ribavirin and interferon (REBETROL®) have resulted in only modest improvements in remission rates and only partial reductions in side effects. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

VX-950, an HCV inhibitor with its structure shown below is such a compound in need. VX-950 is described in PCT Publication Number WO 02/18369, which is incorporated herein by reference in its entirety.

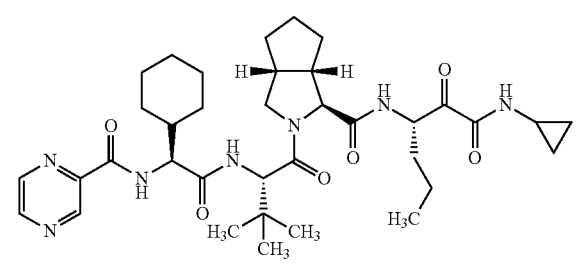 [SMILES: CCC[C@H](NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1]

SUMMARY OF THE INVENTION

In general, the present invention relates to co-crystals comprising the HCV inhibitor VX-950 and a co-crystal former, as well as compositions containing the VX-950 co-crystals. A co-crystal former can be a pharmacologically inert excipient that alters the crystal form of a solid drug through the formation of co-crystals, clathrates, or other crystalline solid forms. It is within the meaning of "co-form" used herein. Under certain circumstances, VX-950 and the co-crystal former together may form a multi-component single phase crystalline solid or composition, i.e., a co-crystal. Compared to their free forms, specific VX-950 co-crystals are advantageous as they may possess improved dissolution, higher aqueous solubility, or greater solid state physical stability than amorphous VX-950 dispersions. The specific VX-950 co-crystals provide a reduced mass of the dosage form and therefore lower pill burden since the VX-950 co-crystals also exhibit higher bulk densities relative to amorphous forms. Further, VX-950 co-crystals provide manufacturing advantages relative to amorphous forms which require spray drying, melt extrusion, lyophilization, or precipitation.

In one aspect, the VX-950 co-crystals provided by this invention contain VX-950 and 2,4-dihydroxybenzoic acid as a co-crystal former compound. In some embodiments, the molar ratio of VX-950 and 2,4-dihydroxybenzoic acid in the co-crystals is in the range of about 5:1 to about 1:5 (e.g., about 1:1). In some embodiments, the co-crystal has at least two of the four X-ray powder diffraction peaks at about 7.6, 8.5, 9.6, and 11.9 degree 2-Theta, each with a standard deviation of about +/−0.3° 2-Theta. In some embodiments, the co-crystal has a peak in its DSC thermogram at about 150.81° C., with a standard deviation of about +/−5° C.

In another aspect, the VX-950 co-crystals provided by this invention contain VX-950 and 2,5-dihydroxybenzoic acid as a co-crystal former compound. In some embodiments, the molar ratio of VX-950 and 2,5-dihydroxybenzoic acid in the co-crystals is in the range of about 5:1 to about 1:5 (e.g., about 1:1). In some embodiments, the co-crystals each have at least two of the four X-ray powder diffraction peaks at about 8.3, 9.6, 11.7, and 17.1 degree 2-Theta, each with a standard deviation of about +/−0.3 degree 2-Theta (i.e., ° 2-Theta). In some other embodiments, the co-crystals have a peak in its DSC thermogram at about 163.48° C. with a standard deviation of about +/−5° C.

In still another aspect, the present invention provides co-crystals comprising VX-950 and 3-methoxy-4-hydroxybenzoic acid as a co-crystal former compound. In some embodiments, the molar ratio of VX-950 and 3-methoxy-4-hydroxybenzoic acid in the co-crystals is in the range of about 5:1 to about 1:5 (e.g., about 1:1). In some embodiments, the co-crystals each have at least two of the four X-ray powder diffraction peaks at about 7.8, 8.6, 11.4, and 11.9 degree 2-Theta, each with a standard deviation of about +/−0.3 degree 2-Theta. In some embodiments, the co-crystals each have a peak in its DSC thermogram at about 178.09° C. with a standard deviation of about +/−5° C.

In another aspect, the invention provides compositions each containing VX-950; a co-crystal former selected from the group consisting of 2,4-dihydroxybenzoic acid, 2,5-dihydroxybenzoic acid, and 3-methoxy-4-hydroxybenzoic acid; and a solvent selected from the group consisting of acetonitrile, dichloromethane, ethyl acetate, ethanol, acetone, or a mixture thereof. In some embodiments, VX-950, the co-crystal former, and the solvent together may take the crystalline form (i.e., forming a co-crystal). Due to the presence of the solvent, the co-crystal may be a solvate. In some other embodiments, the solvent is a mixture of acetonitrile and dichloromethane (e.g., of about 1:1 ratio by volume). In some embodiments, the molar ratio of VX-950 and 4-amino salicylic acid is in the range of about 5:1 to about 1:5 (e.g., about 1:1). In some embodiments, the molar ratio of VX-950 and the solvent is in the range of about 1:0.05 to about 1:1 (e.g., about 1:0.34 or about 1:0.5).

These compositions may have applications, among others, in treating diseases implicated by or associated with HCV. As such, also within the scope of the invention are pharmaceutical compositions each containing VX-950 and a co-crystal former identified above, in an appropriate molar ratio. The pharmaceutical composition may optionally contain a solvent (e.g., acetonitrile, dichloromethane, ethyl acetate, ethanol, or acetone) for forming a solvate. Additionally, the pharmaceutical compositions may further contain a pharmaceutically acceptable diluent, solvent, excipient, carrier, or solubilizing agent.

Still also within the scope of this invention is a method for making a co-crystal described above. The method may include the steps of (a) providing VX-950, (b) providing a co-crystal former selected from the group consisting of 2,4-dihydroxybenzoic acid, 2,5-dihydroxybenzoic acid, and 3-methoxy-4-hydroxybenzoic acid (optionally in a solvent, e.g., ethanol, acetonitrile, dichloromethane, or a mixture thereof, for forming a solvate), (c) grinding, heating, co-subliming, co-melting, or contacting in solution VX-950 with the co-crystal former under crystallization condition so as to form the co-crystal in solid phase, and (d) optionally isolating the co-crystal formed by step (c).

Still within the scope of this invention is a method for modulating a chemical or physical of interest of a co-crystal described above. The method may include the steps of (a) measuring the chemical or physical property of interest for VX-950 and a co-crystal former selected from the group consisting of 2,4-dihydroxybenzoic acid, 2,5-dihydroxybenzoic acid, and 3-methoxy-4-hydroxybenzoic acid, (b) determining the mole fraction of the VX-950 and the co-crystal former that will result in the desired modulation of the chemical or physical property of interest, and (c) preparing the co-crystal with the molar fraction determined in step (b).

The compositions and co-crystals of this invention can be used for treating diseases implicated by or associated with HCV. Thus, also within the scope of this invention is a method of treating such diseases, which comprising administering to a subject in need thereof a therapeutically effective amount of a co-crystal of this invention or a composition of this invention.

The compositions and co-crystals of this invention can also be used as seeds to prepare additional co-crystals containing an active ingredient that can be the same as or different from VX-950, and a co-crystal former that can also be the same as or different from the group consisting of 2,4-dihydroxybenzoic acid, 2,5-dihydroxybenzoic acid, and 3-methoxy-4-hydroxybenzoic acid. For instance, a small amount of a co-crystal of this invention can be placed into a solution containing the desired active ingredient and the co-crystal former and the mixture is allowed to sit so that additional co-crystal can be formed with and grown out of the existing co-crystal.

Additionally, the compositions and co-crystals of this invention can be used as research tools. For instance, they can be used to study the pharmacological properties (such as bioavailability, metabolism, and efficacy) of VX-950 in different form and under condition, or to develop various VX-950 formulations for best delivery and absorption.

DETAILED DESCRIPTION OF THE INVENTION

Figure 1:
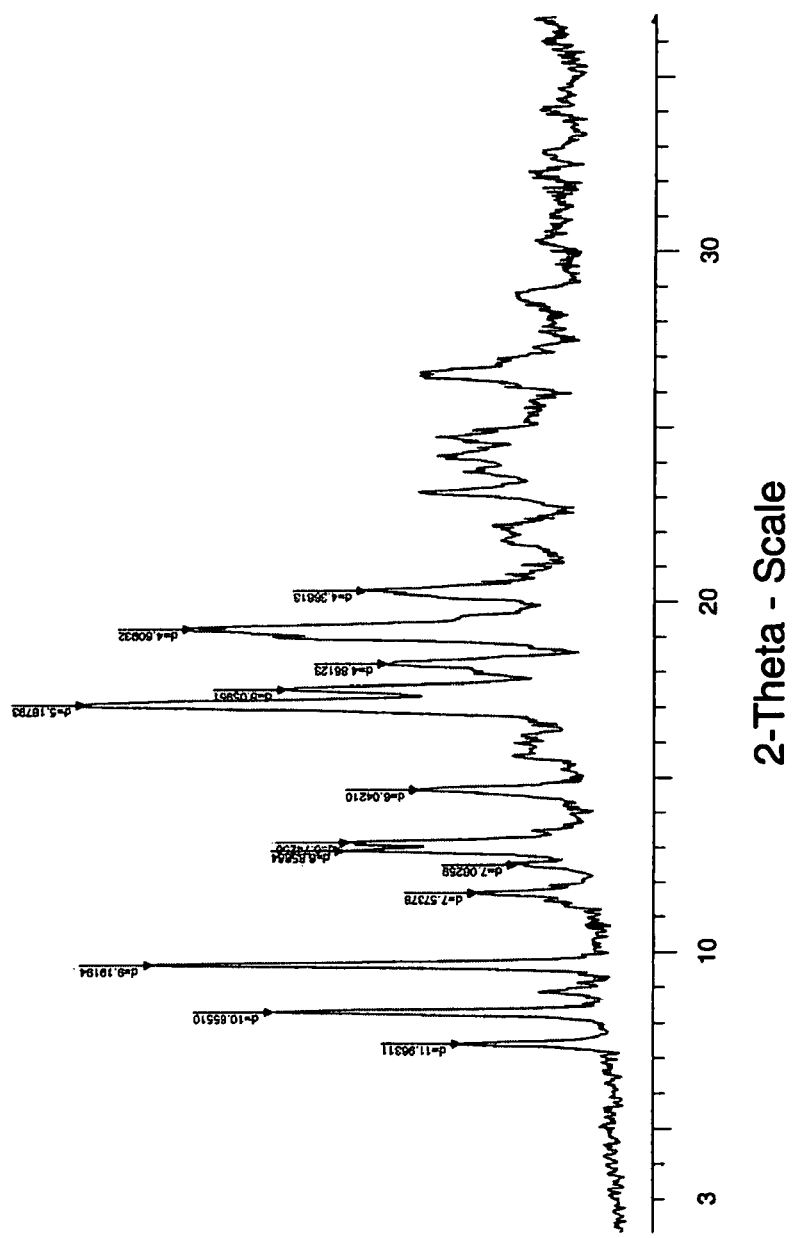
FIG. 1 shows XRPD of the co-crystal of VX-950 and 2,5-dihydroxybenzoic acid.

Methods for preparing and characterizing a co-crystal are well documented in the literature. See, e.g., Trask et al., *Chem. Commun.*, 2004, 890-891; and O. Almarsson and M. J. Zaworotko, *Chem. Commun.*, 2004, 1889-1896. These methods in general are also suitable for preparing and characterizing co-crystals of this invention.

Additionally, the following specific methods can be used to identify co-crystal formers suitable for making co-crystals, particularly the co-crystals of this invention.

Initial identification of or screening for a possible co-crystal former for VX-950 can be conducted on a scale of a few milligrams in a 96-well plate. Visual comparison of the XRPD results to the known crystalline VX-950 diffraction pattern can be used as a screen for new crystal forms and/or altered crystal lattice dimensions that could indicate incorporation of a co-crystal former into a crystal. Oxalic acid, 4-amino salicylic acid, and salicylic acid, etc. have been identified by this initial screening as possible candidates for forming co-crystals with VX-950.

The results of the initial screening can be used for modeling work to identify additional co-crystal formers for VX-950. For instance, due to better physical and chemical properties, 4-amino salicylic acid can be used as a lead molecule in identifying other possible co-crystal formers for VX-950 via molecular modeling. Specifically, a model of 4-ASA can be built using the Quanta software package (Accelrys Inc., San Diego, Calif.) and be complexed with the structure of a single molecule of VX-950 obtained by single crystal x-ray diffraction. The 4-ASA molecule can be placed manually at different positions around VX-950 to form the maximum number of hydrogen bonds between the two molecules. The positional coordinates of the 4-ASA molecule are energy-minimized while the VX-950 molecule is held fixed. An adopted-basis Newton-Raphson method available in Quanta can be used for energy minimization using default settings and a distance-dependent dielectric. AutoNom software (MDL Information Systems, GmbH) can be used to convert the names of chemical compounds in the FDA's EAFUS (Everything Added to Food, US) and GRAS (Generally Regarded As Safe) lists into 2D structures in SMILES format to produce a database of structures. The database can then be searched for new co-crystal formers that fit the pharmacophore identified with 4-ASA. Acceptable pharmacophores have local energy minima similar to that of VX-950 and 4-ASA.

DSC can also be used for screening co-crystal formers. In screening by DSC, physical mixtures of co-crystal formers with VX-950 that showed evidence of solid-phase interactions during DSC (i.e., the formation of eutectic melts) are probably more likely to form co-crystals. To detect an interaction between VX-950 and the co-crystal former, the components can be blended in a 1:1 molar ratio and subjected to a DSC temperature ramp method from the room temperature to, e.g., 300° C. in 10° C. increments. Blends showing a new thermal-event (i.e., an endotherm) that differs in temperature from endotherms of the pure components are selected. When the new thermal transition is observed in addition to that of the one of original components, the molar ratio between VX-950 and the co-crystal former can then be adjusted in an attempt to yield the new thermal transition only. The observed transition temperatures can be plotted as a function of composition to produce phase diagrams for the binary mixtures. Combinations of VX-950 and co-crystal former that produce new thermal transitions on DSC can then be scaled up to produce larger quantities (e.g., grams) as described above.

Mixtures of VX-950 and co-crystal formers with new thermal transitions can be produced in large quantity (i.e., scaled-up), e.g., by using the ball-milling, solvent-evaporation, melting with and without solvents, slurry conversion, blending, sublimation, or modeling. Some of these methods are described in detail below. The products thus prepared can be analyzed or characterized by such known methods as XRPD, TGA, and DSC, and their solubility and stability in an aqueous medium can also be measured by methods known in the art.

Ball-Milling:

Equal molar amounts of VX-950 and a co-crystal former are mixed with an appropriate solvent. The mixture is then milled using a ball-mill apparatus, e.g., Retsch MM200 (GlenMills Inc., Clifton, N.J.) for 3 hours at a frequency of 15 Hz. The mixture is then placed in the milling compartment made of sintered corundum. After milling, the material is placed in a screw cap scintillation vials (uncapped) and dried under vacuum at the room temperature. XRPD and DSC analyses can be performed to characterize the resulting mixture.

Melting in a Reaction Block:

Equi-molar amounts of VX-950 and the co-crystal former are mixed, with or without a solvent. The mixture is then placed in a reaction block, e.g., Model RR98072 by Radleys Discovery Technologies (Essex, UK) with the lid closed and heated to the temperature identified by DSC of the new thermal transition. The mixture is then held for a period of time at the transition temperature before the reaction block is opened and the resulting mixture cooled under ambient conditions.

Solvent Evaporation:

VX-950 and a potential co-crystal former are dissolved separately into a volatile solvent or a solvent mixture (e.g., 50:50 toluene:acetonitrile). Dissolution can be aided by agitation and sonication until a clear solution is obtained. The VX-950 solution is then mixed with the co-crystal former solution in screw-cap scintillation vials at the desired molar ratio. The vials are placed uncapped under reduced pressure and solvent allowed to evaporate to dryness, typically over a period of several days. Solid (crystalline) material is obtained and analyzed.

As mentioned above, co-crystals of this invention can be analyzed by methods known in the art for characterizing solid or crystalline materials. Examples of characterization methods include thermogravimetric analysis (TGA), differential scanning calorimetry (DSC), X-ray powder diffraction (XRPD), solubility analyses, dynamic vapor sorption, infrared off-gas analysis, and suspension stability. TGA can be used to investigate the presence of residual solvents in a co-crystal sample, and to identify the temperature at which decomposition of each co-crystal sample occurs. DSC can be used to look for thermo-transitions occurring in a co-crystal sample as a function of temperature and determine the melting point of each co-crystal sample. XRPD can be used for structural characterization of the co-crystal. Solubility analysis can be performed to reflect the changes in the physical state of each co-crystal sample. And suspension stability analysis can be used to determine the chemical stability of a co-crystal sample in a solvent. Described in great detail are some of such methods.

X-Ray Powder Diffraction (XRPD):

XRPD can be used to characterize the physical form of the material by recording its original pattern and monitoring changes in the pattern with time. The XRPD pattern can be obtained at the room temperature in reflection mode, e.g., by using a Bruker D8 Discover diffractometer that is equipped with a sealed tube source and a Hi-Star area detector (Bruker AXS, Madison, Wis., USA). A copper target X-ray tube (Siemens) can be operated, e.g., at 40 kV and 35 mA. Graphite monochromator and 0.5 mm collimator provided by Bruker can be used to produce parallel, monochromatic beam (CuKa, $\lambda$=1.5418 Å). The distance between the sample and the detector can be approximately 30 cm. The sample can be placed on a Si zero-background wafer (e.g., from The Gem Dugout, State College, Pa.) which is then positioned and centered on XYZ platform. Data can bee acquired using GADDS software for Windows NT, version 4.1.16 (Bruker AXS, Madison, Wis., USA). Two frames can be registered with an exposure time of 120 seconds per frame each at 2 different $2\theta$ angles: 8° and 26° 2-Theta. The sample is oscillated in both X and Y directions with an amplitude of 1 mm during the exposure. The data can then be subsequently integrated over the range of 3° to 41° 2-Theta with a step size of 0.02° 2-Theta and merged into one continuous pattern. Corundum plate (NIST standard 1976) can be used to calibrate the instrument.

Differential Scanning Calorimetry (DSC):

DSC can be used to detect thermal transitions occurring in the sample as a function of temperature and to determine the melting point of crystalline materials. It is performed, e.g., using an MDSC Q100 differential scanning calorimeter (TA Instruments, New Castle, Del.) calibrated with indium. The samples can be prepared in aluminum pans crimped with a single pinhole with the sample size being, e.g., approximately 2 mg. Each run is initially equilibrated to 25° C. followed by a ramp of 10° C./minute to 300° C. VX-950 degrades upon melting, degradation onset is about 240° C. The data can be collected by Thermal Advantage Q Series™ software and analyzed by Universal Analysis software (TA Instruments, New Castle, Del.).

Thermogravimetric Analysis (TGA):

TGA can be used to investigate the presence of residual solvents in the samples, and to identify the temperature at which decomposition of the sample occurs. For instance, a Model Q500 Thermogravimetric Analyzer (TA Instruments, New Castle, Del.) can be used for TGA measurement. The sample can weigh in the range of about 3-8 mg, and be heated at the rate of about 10° C./minute to a final temperature of, e.g., 300° C. The data can be, e.g., collected by Thermal Advantage Q Series™ software and analyzed by Universal Analysis software (TA Instruments, New Castle, Del.).

Fourier Transform Infrared (FT-IR) Spectrometry:

FT-IR can be used to investigate hydrogen bonding in blends of VX-950 with a co-crystal former at different molar ratios. Infrared transmission spectra can be obtained, e.g., from KBr pellets with Nexus 670 spectrometer (Thermo Electron Corp.; Madison, Wis.) from 4000 to 625 $cm^{-1}$.

Solubility Determination:

Solubility can be expressed in VX-950 equivalents. It can be measured to reflect the changes in the physical state of the material, and to monitor progress toward the goal of enhancing VX-950 solubility. Specifically, an aliquot of the material can be placed in an aqueous medium with a target solubility of 10 mg/mL. At set time points, aliquots of supernatant are withdrawn, filtered through a 0.45 micron filter (e.g., Millex; Millipore, Billerica, Mass.) and analyzed using HPLC (e.g., Agilent 1100; Palo Alto, Calif.). The samples are run isocratically with the detector, e.g., set at 270 nm and a flow rate of 1 mL/min on an XTerra® Phenyl column 150 mm×4.6 mm, 3.5 µm particle size (P/N 186001144) (Waters Corp., Milford, Mass.). The mobile phase contained potassium phosphate buffer (10 mM, pH=7.0) and methanol in a 60:40 (v/v) ratio. The concentrations of VX-950 can be determined by comparing chromatographic peak areas with a calibration curve produced using standards of known concentration.

Hotstage Microscopy:

Microscope images can be taken, e.g., with an Olympus BX51 confocal microscope with polarized films, an SLM-Plan 50× infinity corrected objective, a C-5050 digital camera, and an Instec hotstage with a variable temperature controller. The experimental procedure consists of a linear heating ramp between different temperature steps in which the samples are allowed to equilibrate for several minutes. Digital images are collected manually throughout the ramp to capture any transitions that occurred.

An effective amount of co-crystals or compositions of this invention, each including VX-950 and a co-crystal former (e.g., 4-hydroxybenzoic acid, 4-amino salicylic acid (with acetonitrile), phenyl alanine, threonine, adipic acid, succinic acetate, praline, methyl 4-hydroxybenzoate, anthranilic acid, d-Biotin, or tartaric acid) can be used to treat diseases implicated or associated with the HCV. An effective amount is the amount which is required to confer a therapeutic effect on the treated subject, e.g. a patient. The effective amount of a co-crystal of VX-950 and the co-crystal former is between about 0.1 mg/kg to about 150 mg/kg (e.g., from about 1 mg/kg to about 60 mg/kg). Effective doses will also vary, as recognized by those skilled in the art, dependent on route of administration, excipient usage, and the possibility of co-usage with other therapeutic treatments including use of other therapeutic agents and/or therapy.

The co-crystals or pharmaceutical compositions of this invention can be administered to the subject in need thereof (e.g., cells, a tissue, or a patient (including an animal or a human)) by any method that permits the delivery of the compound VX-950, e.g., orally, intravenously, or parenterally. For instance, they can be administered via pills, tablets, capsules, aerosols, suppositories, liquid formulations for ingestion or injection or for use as eye or ear drops, dietary supplements, and topical preparations.

The pharmaceutical compositions can include diluents, solvents, excipients and carriers such as water, Ringer's solution, isotonic saline, 5% glucose, and isotonic sodium chloride solution. In another embodiment, the pharmaceutical composition can further include a solubilizing agent such as cyclodextrin. Additional examples of suitable diluents, solvents, excipients, carriers, and solubilizing agents can be found, e.g., in U.S. Pharmacopeia 23/National Formulary 18, Rockville, Md., U.S. Pharmacopeia Convention, Inc., (1995); Ansel H C, Popovich N G, Allen Jr L V. *Pharmaceutical Dosage Forms and Drug Delivery Systems*, Baltimore Md., Williams & Wilkins, (1995); Gennaro A R., Remingtons: *The Science and Practice of Pharmacy*, Easton Pa., Mack Publishing Co., (1995); Wade, A., Weller, P. J., *Handbook of*

*Pharmaceutical Excipients,* 2nd Ed, Washington D.C., American Pharmaceutical Association, (1994); Baner G S, Rhodes C T. Modern Pharmaceutics, 3rd Ed., New York, Marcel Dekker, Inc., (1995); Ranade V V, Hollinger Mass., *Drug Delivery Systems*, Boca Raton, CRC Press, (1996).

The pharmaceutical compositions can also include aqueous solutions of the co-crystal, in an isotonic saline, 5% glucose or other well-known pharmaceutically acceptable excipient(s). Solubilizing agents such as cyclodextrins, or other solubilizing agents well-known to those familiar with the art, can be utilized as pharmaceutical excipients for delivery of the therapeutic compound VX-950. As to route of administration, the co-crystals or pharmaceutical compositions can be administered orally, intranasally, transdermally, intradermally, vaginally, intraaurally, intraocularly, buccally, rectally, transmucosally, or via inhalation, or intravenous administration. The compositions may be delivered intravenously via a balloon catheter. The compositions can be administered to an animal (e.g., a mammal such as a human, non-human primate, horse, dog, cow, pig, sheep, goat, cat, mouse, rat, guinea pig, rabbit, hamster, gerbil, ferret, lizard, reptile, or bird).

The co-crystals or pharmaceutical compositions of this invention also can be delivered by implantation (e.g., surgically) such with an implantable device. Examples of implantable devices include, but are not limited to, stents, delivery pumps, vascular filters, and implantable control release compositions. Any implantable device can be used to deliver the compound VX-950 as the active ingredient in the co-crystals or pharmaceutical compositions of this invention, provided that 1) the device, compound VX-950 and any pharmaceutical composition including the compound are biocompatible, and 2) that the device can deliver or release an effective amount of the compound to confer a therapeutic effect on the treated patient.

Delivery of therapeutic agents via stents, delivery pumps (e.g., mini-osmotic pumps), and other implantable devices is known in the art. See, e.g., "Recent Developments in Coated Stents" by Hofma et al., published in *Current Interventional Cardiology Reports,* 2001, 3: 28-36, the entire contents of which, including references cited therein, are incorporated herein. Other descriptions of implantable devices, such as stents, can be found in U.S. Pat. Nos. 6,569,195 and 6,322, 847, and PCT International Publication Numbers WO 2004/044405, WO 2004/018228, WO 2003/229390, WO 2003/228346, WO 2003/225450, WO 2003/216699, WO 03/0204168, WO 2008/098255 A2, WO 2008/027872 A2, WO 2008/027871 A2, WO 2007/140320 A2, WO 2006/124823A2, WO 2007/128969 A2, WO 2007/030478 A2, and WO 2005/120393 A2, each of which (as well as other publications cited herein) is incorporated herein in its entirety.

Described below are examples of preparing and characterizing co-crystals of this invention, which are meant to be only illustrative and not to be limiting in any way.

Example 1

Preparation by Ball-Milling Method

VX-950 and an equal molar equivalent of a co-crystal former (e.g., 2,4-dihydroxybenzoic acid or 3-methoxy-4-hydroxybenzoic acid) can be mixed with a solvent (e.g., methyl ethyl ketone or ethyl acetate). The components can then be milled using a Wig-L-Bug apparatus, e.g., Retsch MM200 (GlenMills Inc, Clifton, N.J.) for 10 minutes at the frequency of 15 Hz. After milling, a batch is dried, e.g., in a vacuum oven at 75° C. for 2 hours, to give a co-crystal of the invention.

Example 2

Preparation by Melting Method

VX-950 and an equal molar equivalent of a co-crystal former (e.g., 2,4-dihydroxybenzoic acid or 3-methoxy-4-hydroxybenzoic acid) can be mixed, e.g., by vortex for 5 minutes, with or without a solvent. The mixture is then placed in a reaction block (e.g., RR 98072 from Radley Discovery Technologies) with the lid closed and heated to the endotherm. The mixture is held for 30 minutes at the endotherm temperature, and then the resulting mixture was cooled off under ambient conditions with the lid off, and the solvent, when used, removed to give a co-crystal of the invention.

Example 3

Preparation by Solvent-Evaporation Method 2,4-Dihydroxybenzoic acid 200 mg of VX-950 and 80 mg of 2,4-dihydroxybenzoic acid (Sigma Chemicals Co., St. Louis, Mo., USA) were charged into a 20 mL glass vial. To the vial were then added 100 µL of dichloromethane and 100 µL of acetonitrile. The vial containing the mixture was capped and the mixture was stirred at the room temperature with a magnetic stir bar at 600 rpm for 16 hours. The crystalline solid was isolated and the liquid on its surface was removed by filter paper to give a co-crystal of VX-950 and 2,4-dihydroxybenzoic acid.

3-Methoxy-4-hydroxybenzoic acid 200 mg of VX-950 and 80 mg of 3-methoxy-4-hydroxybenzoic acid (Sigma Chemicals Co., St. Louis, Mo., USA) were charged into a 20 mL glass vial. To the vial were then added 100 µL of dichloromethane and 100 µL of acetonitrile. The vial containing the mixture was capped and the mixture was stirred at the room temperature with a magnetic stir bar at 600 rpm for 72 hours. The crystalline solid was isolated and the liquid on its surface was removed by filter paper to give a co-crystal of VX-950 and 3-methoxy-4-hydroxybenzoic acid.

2,5-Dihydroxbenzoic acid 200 mg of VX-950 and 80 mg of 2,5-dihydroxybenzoic acid (Sigma Chemicals Co., St. Louis, Mo., USA) were charged into a 20 mL glass vial. To the vial were then added 100 µL of dichloromethane and 100 µL of acetonitrile. The vial containing the mixture was capped and the mixture was stirred at the room temperature with a magnetic stir bar at 600 rpm for 16 hours. The crystalline solid was isolated and the liquid on its surface was removed by filter paper to give a co-crystal of VX-950 and 2,5-dihydroxybenzoic acid.

Example 4

Single Crystal Diffraction

Single crystal diffraction of the co-crystals can be performed on a Bruker APEX II CCD diffractometer at 100K using Cu Kα radiation by using single crystals picked from mother liquors and mounted on glass fibers. The crystals are cooled to 100K in a nitrogen flow system and oscillation photos were taken around ω axis at 4 φ angles. The data are indexed, integrated, and scaled with the APEX software. The structures can be solved and refined with the SHELX-TL package.

Example 5

Thermogravimetric Analysis (TGA)

TGA of each sample was performed using a Model Q500 Thermogravimetric Analyzer (TA Instruments, New Castle, Del., USA), which uses its control Thermal Advantage Q Series™ software, Version 2.2.0.248, Thermal Advantage Release 4.2.1 (TA Instruments-Water LLC), with the following components: QAdv.exe version 2.2 build 248.0; RhDII.dII version 2.2 build 248.0; RhBase.dII version 2.2 build 248.0; RhComm.dII version 2.2 build 248.0; TaLicense.dII version 2.2 build 248.0; and TGA.dII version 2.2 build 248.0. In addition, the analysis software used was Universal Analysis 2000 software for Windows 2000/XP, version 4.1 D build 4.1.0.16 (TA Instruments).

For all of the experiments, the basic procedure for performing TGA included transferring an aliquot (about 3-8 mg) of a sample into a platinum sample pan (Pan: Part No. 952018.906, TA Instruments). The pan was placed on a loading platform and was then automatically loaded into the Q500 Thermogravimetric Analyzer using the control software. Thermograms were obtained by individually heating the sample at 10° C./minute across a temperature range (generally from the room temperature to 400° C. under flowing dry nitrogen (compressed nitrogen, grade 4.8 (BOC Gases, Murray Hill, N.J., USA), with a sample purge flow rate of 90 L/minute and a balance purge flow rate of 10 L/minute. Thermal transitions (e.g. weight changes) were viewed and analyzed using the analysis software provided with the instrument.

Figure 2:
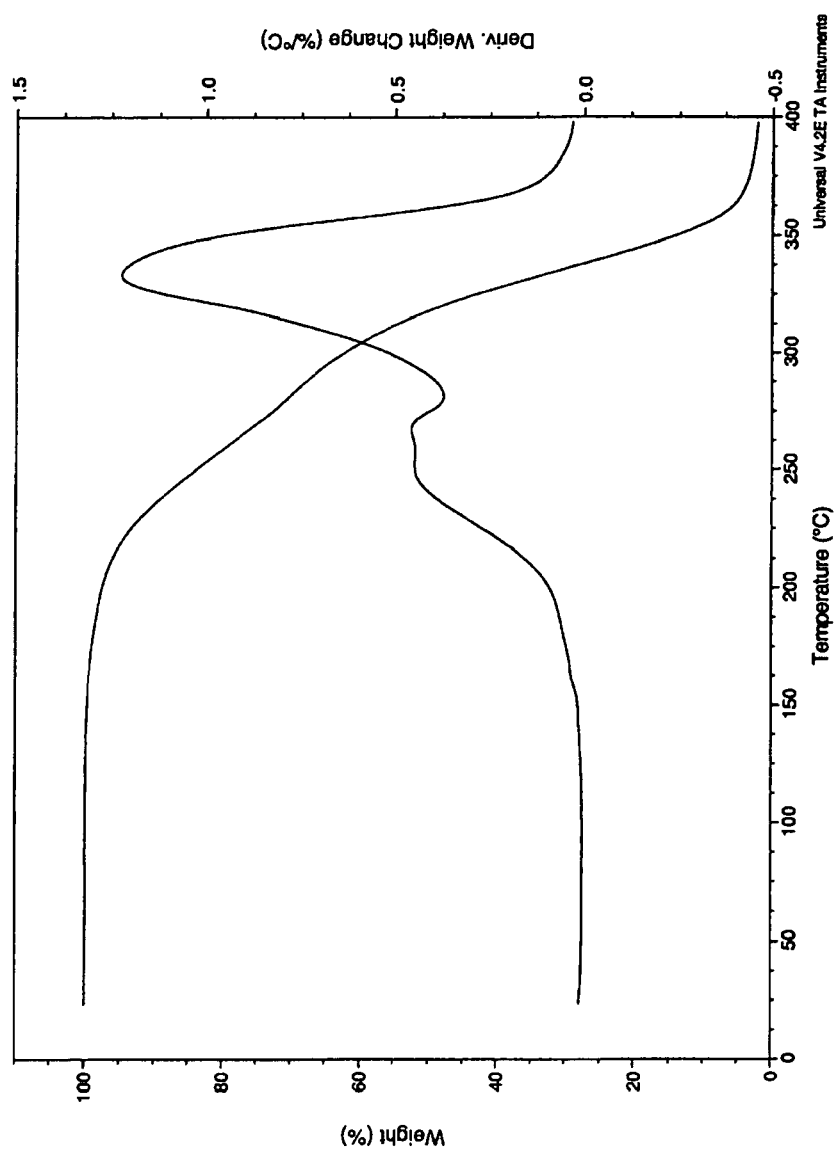
FIG. 2 shows a TGA spectrum of the co-crystal of VX-950 and 2,5-dihydroxybenzoic acid.

As in FIG. 2, the TGA spectrum of the co-crystal of VX-950 and 2,5-dihydroxybenzoic acid (molar ratio being 1) showed approximate showed continuous weight loss from approximately 210° C.

Figure 5:
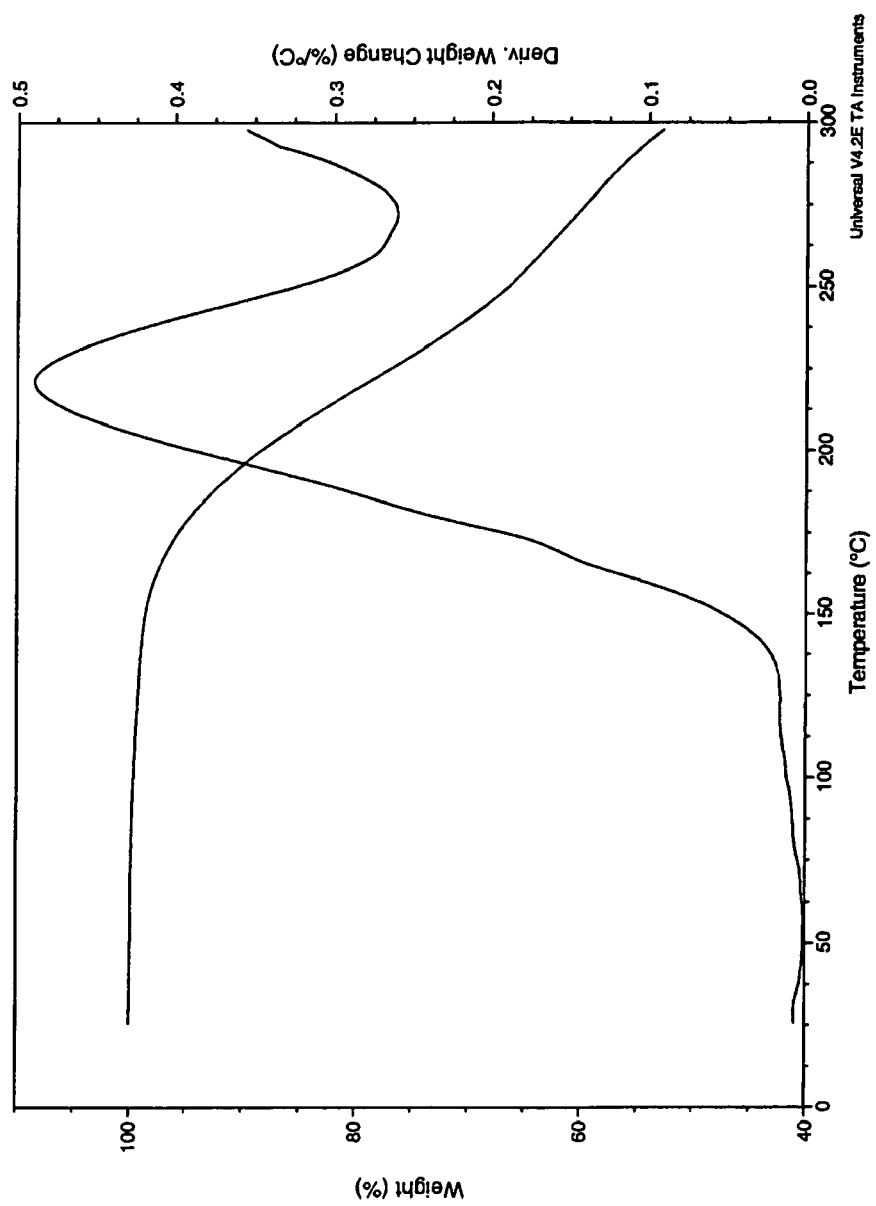
FIG. 5 shows a TGA spectrum of the co-crystal of VX-950 and 3-methoxy-4-hydroxybenzoic acid.

As in FIG. 5, the TGA spectrum of the co-crystal of VX-950 and 3-methoxy-4-hydroxybenzoic acid (molar ratio also being 1) showed continuous weight loss from approximately 155° C.

Figure 8:
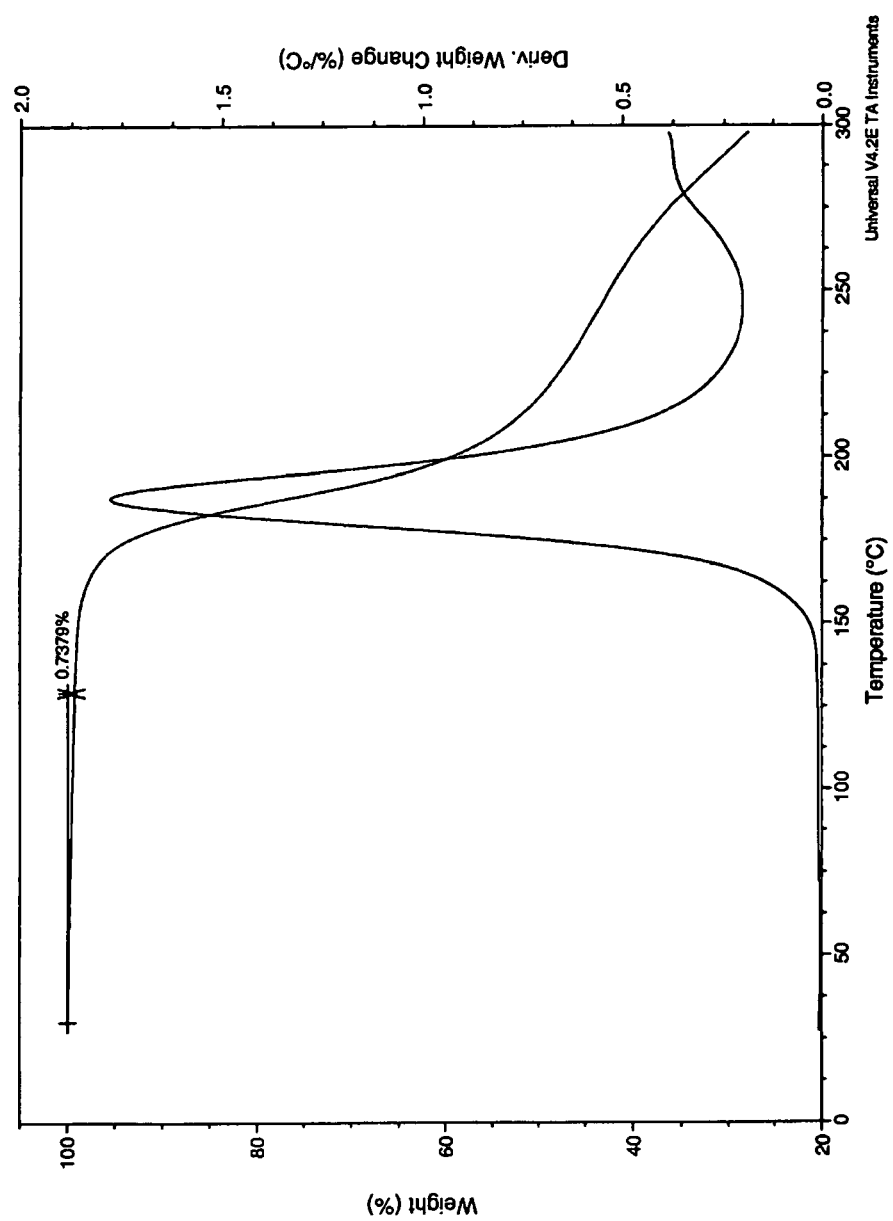
FIG. 8 shows a TGA spectrum of the co-crystal of VX-950 and 2,4-dihydroxybenzoic acid.

As in FIG. 8, the TGA spectrum of the co-crystal of VX-950 and 2,4-dihydroxybenzoic acid showed continuous weight loss from approximately 165° C.

Example 6

Differential Scanning Calorimetry (DSC)

DSC analysis was performed using an MDSC Q100 Differential Scanning Calorimeter (TA Instruments), which uses its control Thermal Advantage Q Series™ software, version 2.2.0.248, Thermal Advantage Release 4.2.1, with the following components: QAdv.exe version 2.2 build 248.0; RhDII.dII version 2.2 build 248.0; RhBase.dII version 2.2 build 248.0; RhComm.dII version 2.2 build 248.0; TaLicense.dII version 2.2 build 248.0; and DSC.dII version 2.2 build 248.0. In addition, the analysis software used was Universal Analysis 2000 software for Windows 2000/XP, version 4.1 D build 4.1.0.16 (TA Instruments). The instrument was calibrated with indium.

For all DSC analysis, an aliquot of a sample (approximately 2 mg) was weighed into an aluminum sample pan (Pan: Part No. 900786.901; and Lid: Part No. 900779.901, TA Instruments). The sample pan was closed by crimping with a single pinhole, allowed to equilibrate at 30° C., and then loaded into the Q100 Differential Scanning Calorimeter which was equipped with an autosampler. A thermogram was obtained by individually heating each sample at a rate at 50° C./minute across a temperature range (generally from the room temperature to 400° C.) under flowing dry nitrogen (compressed nitrogen, grade 4.8 (BOC Gases, Murray Hill, N.J., USA), with a sample purge flow rate of 60 L/minute and a balance purge flow rate of 40 L/minute. An empty aluminum pan prepared the same way as the pan with the sample was used a reference. Thermal transitions were viewed and analyzed using the analysis software provided with the instrument.

Figure 3:
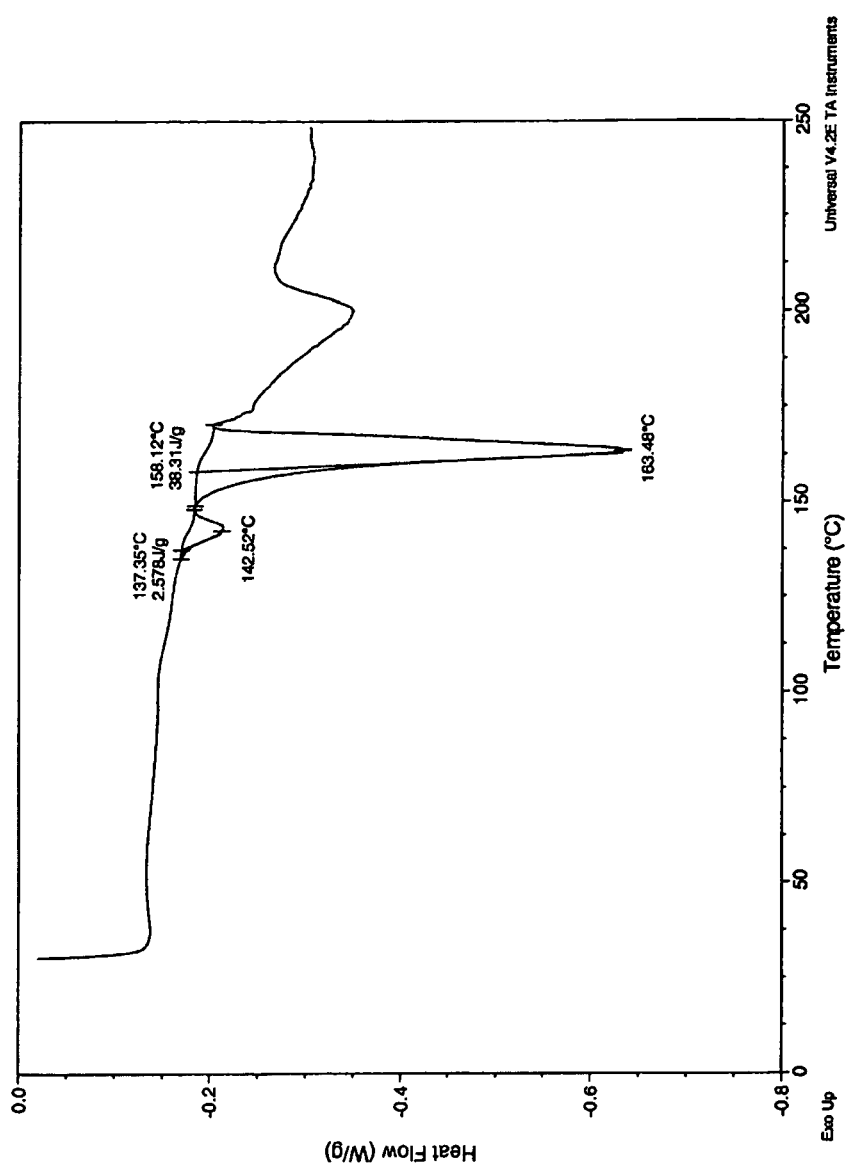
FIG. 3 shows a DSC spectrum of the co-crystal of VX-950 and 2,5-dihydroxybenzoic acid.

As in FIG. 3, the DSC thermogram shows the co-crystal of VX-950 and 2,5-dihydroxybenzoic acid (molar ratio being 1:1) melt at approximately 163.48° C.

Figure 6:
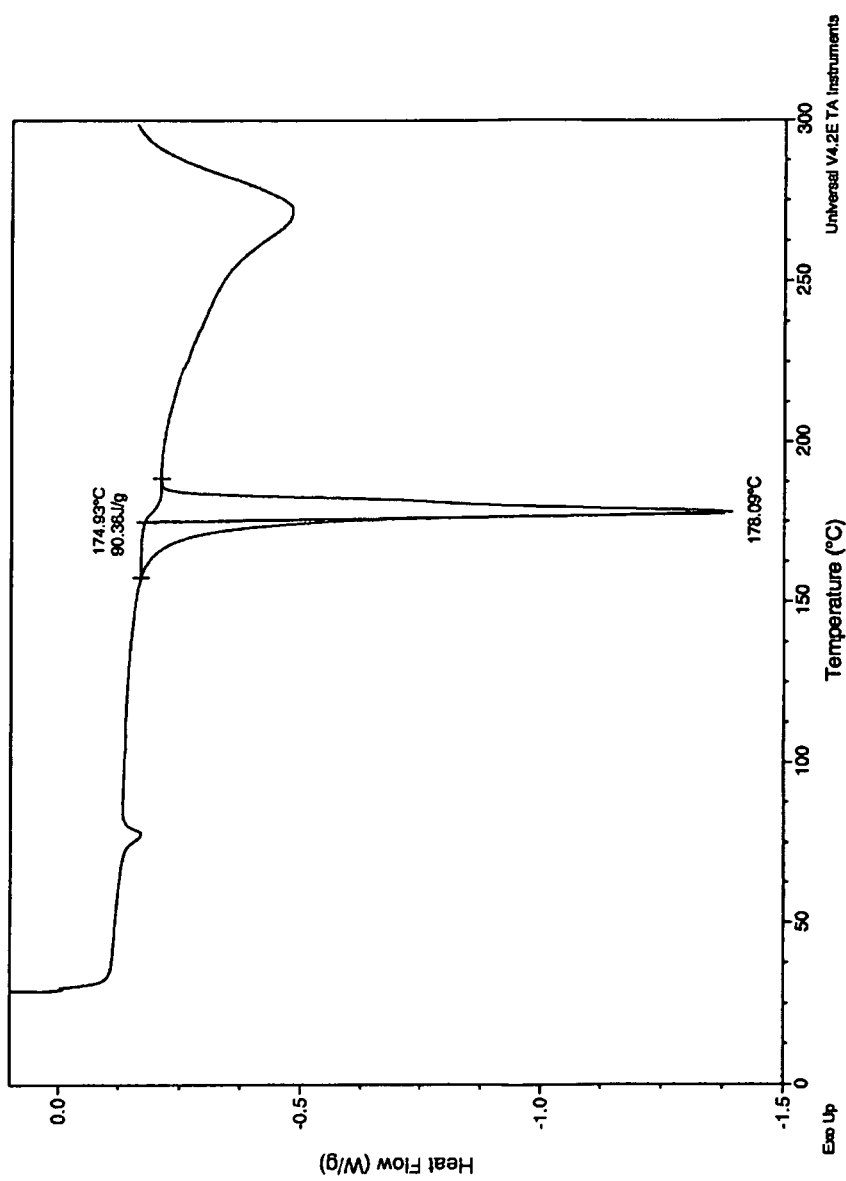
FIG. 6 shows a DSC spectrum of the co-crystal of VX-950 and 3-methoxy-4-hydroxybenzoic acid.
Figure 7:
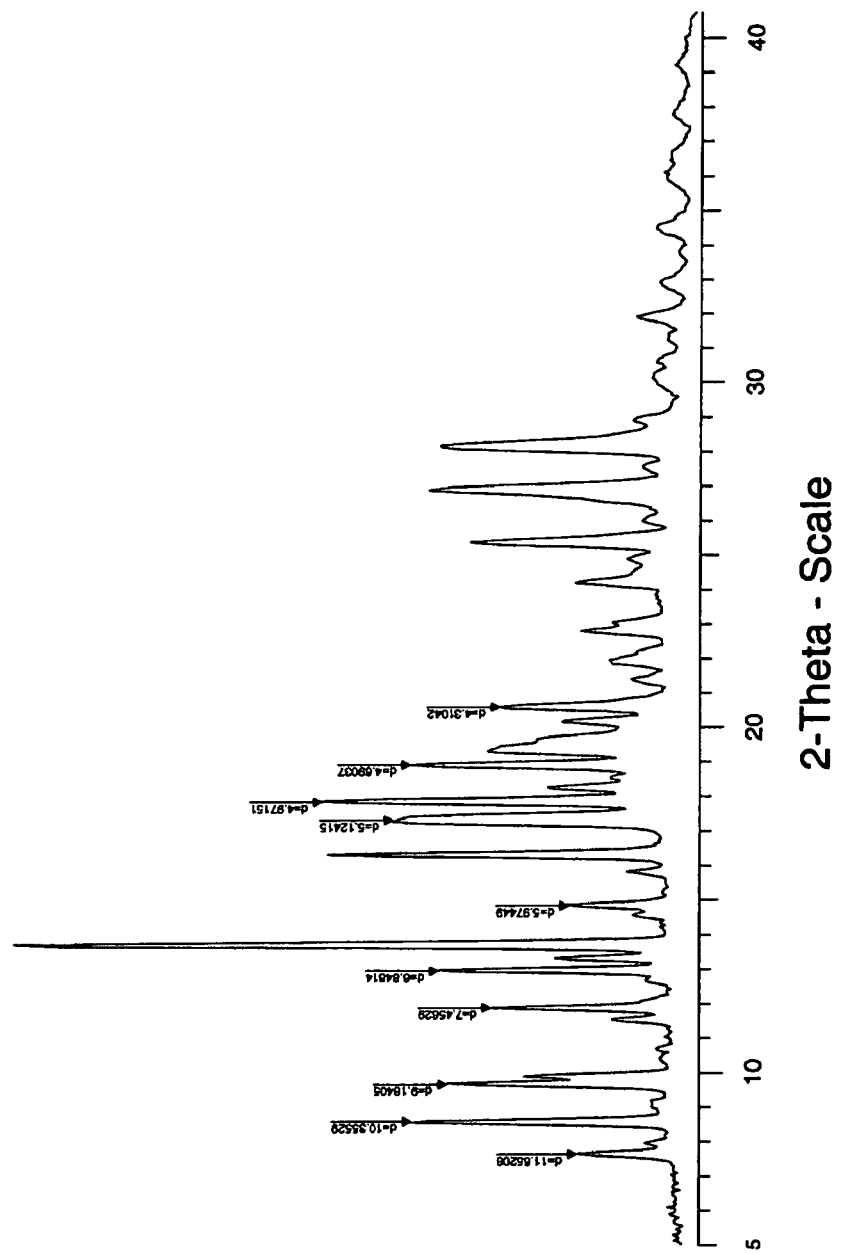
FIG. 7 shows XRPD of the co-crystal of VX-950 and 2,4-dihydroxybenzoic acid.

As in FIG. 6, the DSC thermogram shows the co-crystal of VX-950 and 3-methoxy-4-hydroxybenzoic acid (molar ratio being 1:1) melt at approximately 178.09° C.

Figure 9:
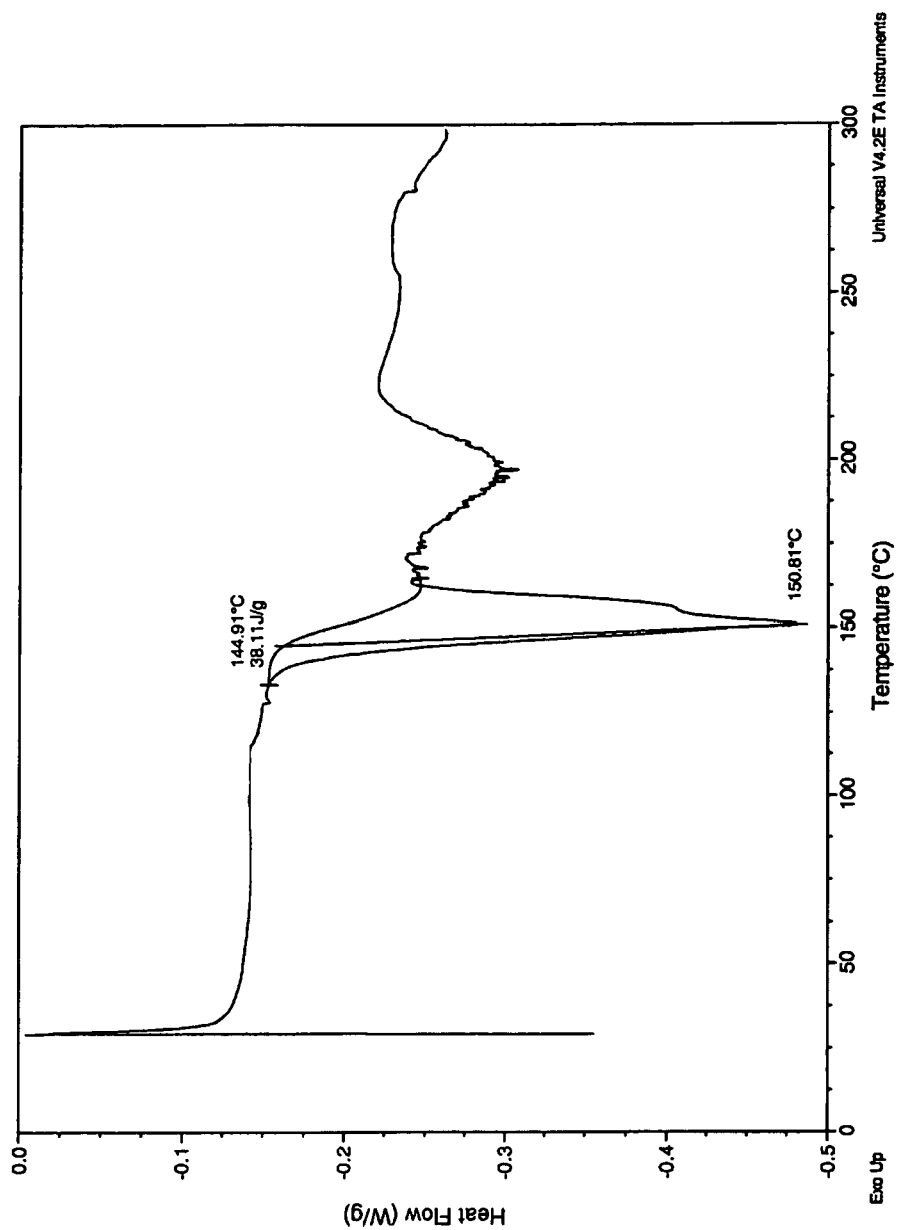
FIG. 9 shows a DSC spectrum of the co-crystal of VX-950 and 2,4-dihydroxybenzoic acid.

As in FIG. 9, the DSC thermogram shows the co-crystal of VX-950 and 2,4-dihydroxybenzoic acid (molar ratio being 1:1) as an acetonitrile solvate melt at about 150.81° C.

Example 7

X-Ray Powder Diffraction (XRPD)

The XRPD pattern was obtained at the room temperature in reflection mode by using a Bruker D8 Discover diffractometer that was equipped with a sealed tube source and a Hi-Star area detector (Bruker AXS, Madison, Wis., USA). A copper target X-ray tube (Siemens) was operated at 40 kV and 35 mA. Graphite monochromator and 0.5 mm collimator provided by Bruker were used to produce parallel, monochromatic beam (CuKa, λ=1.5418 Å). The distance between the sample and the detector was approximately 30 cm. The sample was placed on a Si zero-background wafer (The Gem Dugout, State College, Pa.) which was then positioned and centered on XYZ platform. Data were acquired using GADDS software for Windows NT, version 4.1.16 (Bruker AXS, Madison, Wis., USA). Two frames were registered with an exposure time of 120 seconds per frame each at 2 different 2θ angles: 8° and 26°. The sample was oscillated in both X and Y directions with an amplitude of 1 mm during the exposure. The data were subsequently integrated over the range of 3° to 41° 2-Theta with a step size of 0.02° and merged into one continuous pattern. Corundum plate (NIST standard 1976) was used to calibrate the instrument.

As shown in FIG. 1, the XRPD pattern of the co-crystal of VX-950 and 2,5-dihydroxybenzoic acid (molar ratio being 1:1) showed peaks at about 8.292, 9.614, 11.675, 12.488, 12.897, 13.120, 14.649, 17.078, 17.514, 18.235, 19.241, and 20.323 degree 2-Theta.

Figure 4:
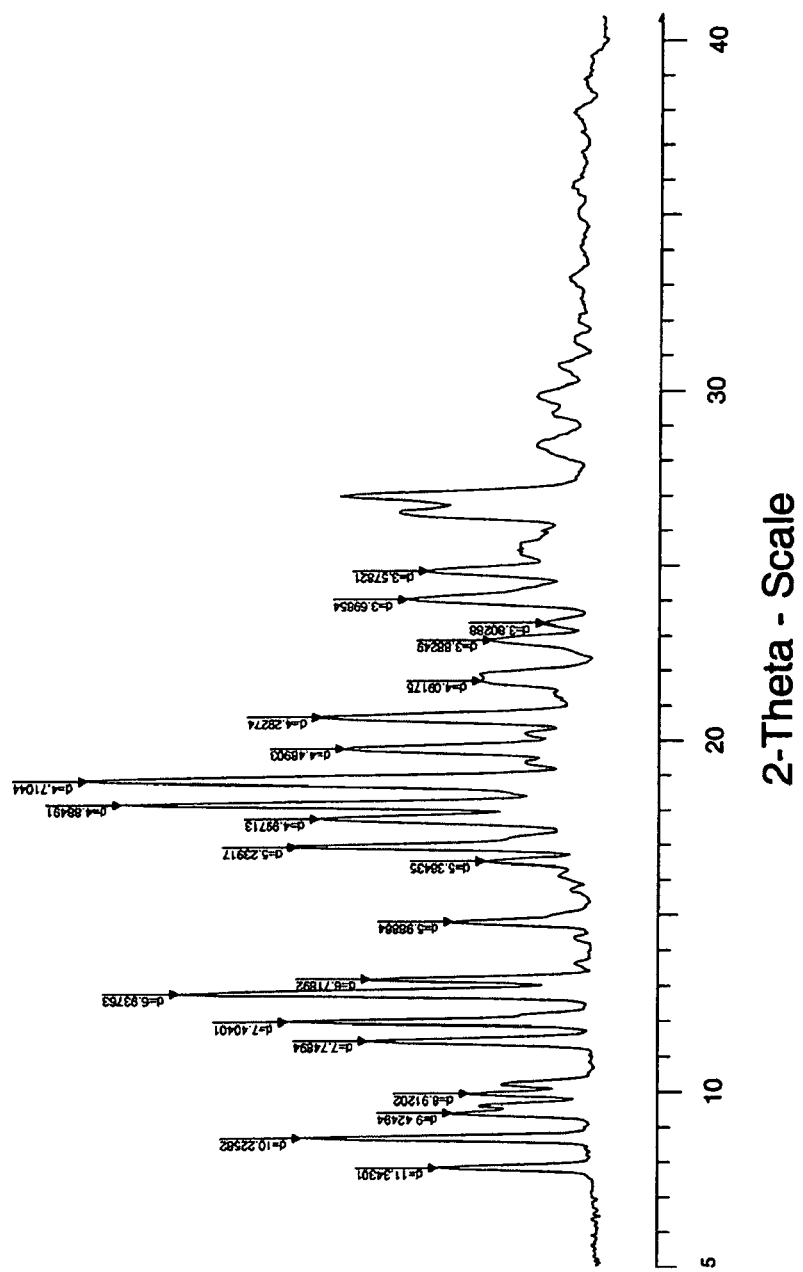
FIG. 4 shows XRPD of the co-crystal of VX-950 and 3-methoxy-4-hydroxybenzoic acid.

As shown in FIG. 4, the XRPD pattern of the co-crystal of VX-950 and 3-methoxy-4-hydroxybenzoic acid (molar ratio being 1:1) showed peaks at about 7.788, 8.640, 9.376, 9.917, 11.410, 11.943, 12.749, 13.166, 14.780, 16.512, 16.909, 17.734, 18.145, 18.823, 19.761, 20.674, 21.702, 22.887, 23.372, 24.042, and 24.863 degree 2-Theta.

As shown in FIG. 8, the XRPD pattern of the co-crystal of VX-950 and 2,4-dihydroxybenzoic acid (molar ratio being 1:1) showed peaks at about 7.581, 8.532, 9.622, 11.859, 12.920, 14.815, 17.291, 17.827, 18.905, and 20.588 degree 2-Theta.

Example 8

Solubility Analyses

An aliquot of a co-crystal of this invention can be placed in a tube and then an aqueous medium is added. At set time points, an aliquot of supernatant is withdrawn, filtered through 0.45 PTFE micron filter (Millex, LCR, Millipore) and processed for high performance liquid chromatography (HPLC) analysis (Agilent 1100; Palo Alto, Calif., USA). The system is equipped with an autosampler set at 25° C. For the sample handling, an aliquot of the co-crystal can be diluted with acetonitrile at 1 to 1 by v/v ratio. The samples can be run isocratically with the detector set at 270 nm with a column being XTerra® Phenyl column 150 mm×4.6 mm, 3.5 μm Particle Size (P/N 186001144) (Waters, Milford, Mass., USA). The mobile phase can be potassium phosphate buffer (10 mM, pH=7.0):methanol at 60:40 (v/v) ratio. The run can be done at the flow-rate of 1 mL/minute and completed within 15 minutes.

The water solubility data can be determined at ambient conditions by equilibrating the co-crystal with water on a shaking bed for 24 hours followed by centrifugation and separation of the saturated solution. The solubility in simulated gastric and intestinal fluids (both fed and fasted) can be determined at room temperature by adding the co-crystal to the simulated fluid under continuous stirring for 24 hours. At selected time points, samples are filtered and the filtrate assayed by HPLC.

Example 9

Suspension Stability

The physical stability of a co-crystal of this invention upon suspension in aqueous media can also evaluated. Specifically, the co-crystal powder can be slurried, e.g., in (1) unbuffered, deionized water and (2) a 1% (w/w) solution of HPMC (low viscosity grade) at 25° C. at a nominal concentration of approximately 6 mg/mL. Slurries can then mixed using a magnetic stir bar and plate. The samples of the solid can be isolated by filtration, e.g., at time intervals of 1, 2, 6 and 24 hours.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A co-crystal of

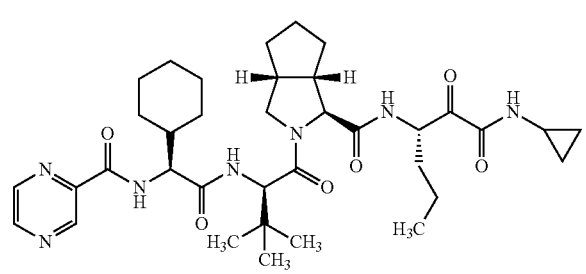 [SMILES: CCC[C@H](NC(=O)[C@@H]1[C@H]2CCC[C@H]2CN1C(=O)[C@H](NC(=O)[C@@H](NC(=O)c1cnccn1)C1CCCCC1)C(C)(C)C)C(=O)C(=O)NC1CC1]

and 2,5-dihydroxybenzoic acid, wherein said co-crystal has at least two of the four X-ray powder diffraction peaks at about 8.9, 9.6, 11.7, and 17.1 degree 2-Theta, each with a standard deviation of about +/−0.3 degree 2-Theta.

2. The co-crystal of claim 1, wherein the molar ratio of

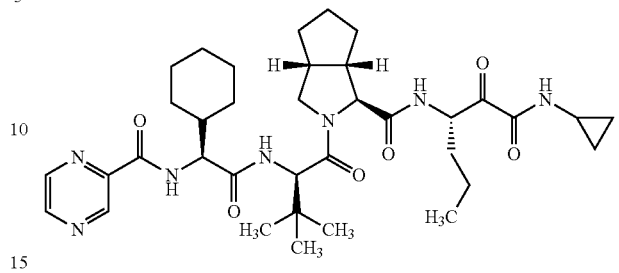

and 2,5-dihydroxybenzoic acid is in the range of about 5:1 to about 1:5.

3. The co-crystal of claim 1, wherein the molar ratio of

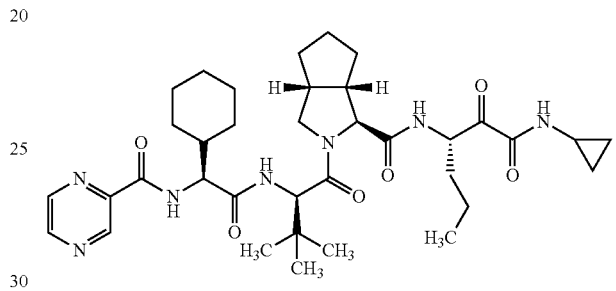

and 2,5-dihydroxybenzoic acid is about 1:1.

4. The co-crystal of claim 1, having a peak in its DSC thermogram at about 163.48° C. with a standard deviation of about +/−5° C.

5. A co-crystal of

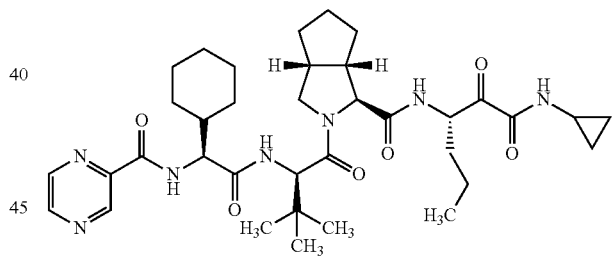

and 2,4-dihydroxybenzoic acid, wherein said co-crystal has at least two of the four X-ray powder diffraction peaks at about 8.9, 9.6, 11.7, and 17.1 degree 2-Theta, each with a standard deviation of about +/−0.3 degree 2-Theta.

6. The co-crystal of claim 5, wherein the molar ratio of

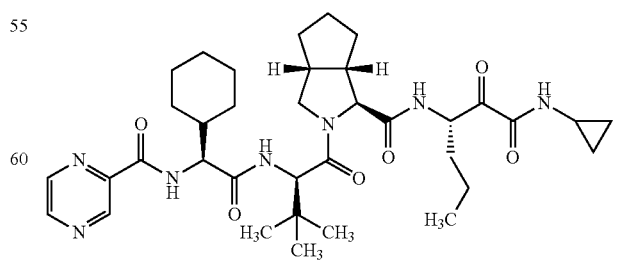

and 2,4-dihydroxybenzoic acid is in the range of about 5:1 to about 1:5.

7. The co-crystal of claim 5, wherein the molar ratio of
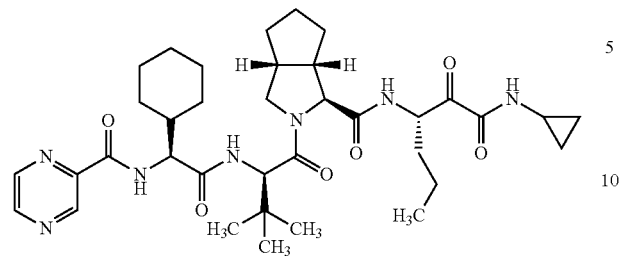
and 2,4-dihydroxybenzoic acid is about 1.1.
8. The co-crystal of claim 5, having a peak in its DSC thermogram at about 150.81° C. with a standard deviation of about +/−5° C.
* * * * *